US009737258B2

(12) United States Patent
Poon et al.

(10) Patent No.: US 9,737,258 B2
(45) Date of Patent: Aug. 22, 2017

(54) SYSTEMS AND METHODS FOR DETECTING A PHYSIOLOGICAL ABNORMALITY IN A PATIENT BY USING CARDIAC OR OTHER CHAOS IN COMBINATION WITH NON-INCREASING PARASYMPATHETIC MODULATION

(71) Applicant: Massachusetts Institute of Technology, Cambridge, MA (US)

(72) Inventors: Chi-Sang Poon, Lexington, MA (US); Zhi-De Deng, Brooklyn, NY (US)

(73) Assignee: Massachusetts Institute of Technology, Cambridge, MA (US)

( * ) Notice: Subject to any disclaimer, the term of this patent is extended or adjusted under 35 U.S.C. 154(b) by 244 days.

(21) Appl. No.: 13/755,345

(22) Filed: Jan. 31, 2013

(65) Prior Publication Data

US 2014/0213919 A1 Jul. 31, 2014

(51) Int. Cl.
*A61B 5/04* (2006.01)
*A61B 5/00* (2006.01)
*A61B 5/0205* (2006.01)
*A61B 5/0456* (2006.01)
*A61B 5/1455* (2006.01)
*A61B 5/024* (2006.01)
*G06F 19/00* (2011.01)
(Continued)

(52) U.S. Cl.
CPC .......... *A61B 5/4818* (2013.01); *A61B 5/0205* (2013.01); *A61B 5/02405* (2013.01); *A61B 5/04012* (2013.01); *A61B 5/0456* (2013.01); *A61B 5/14551* (2013.01); *A61B 5/4035* (2013.01); *A61B 5/4812* (2013.01); *A61B 5/7275* (2013.01); *A61B 5/743* (2013.01); *A61B 5/7405* (2013.01); *A61B 5/746* (2013.01); *G06F 19/345* (2013.01); *A61B 5/1102* (2013.01); *A61B 5/1455* (2013.01); *G06K 9/0053* (2013.01)

(58) Field of Classification Search
CPC .............. A61B 5/0402; A61B 5/02405; A61B 5/04012; A61B 5/0245; A61B 5/4818; A61B 5/0205; A61B 5/0456; A61B 5/4035; A61B 5/4812; A61B 5/7405; A61B 5/7275; A61B 5/746
USPC .......................... 600/508, 509, 513–518, 521
See application file for complete search history.

(56) References Cited

U.S. PATENT DOCUMENTS 5,792,062 A 8/1998 Poon et al.
5,797,840 A 8/1998 Akselrod et al.
5,938,594 A 8/1999 Poon et al.
(Continued)

FOREIGN PATENT DOCUMENTS

WO WO 2004/086967 A1 10/2004

OTHER PUBLICATIONS

PCT Search Report and Written Opinion of the ISA dated Mar. 17, 2014; for PCT Pat. App. No. PCT/US2013/075577; 13 pages.
(Continued)

*Primary Examiner* — Michael Kahelin
*Assistant Examiner* — Minh Duc Pham
(74) *Attorney, Agent, or Firm* — Daly, Crowley, Mofford & Durkee, LLP

(57) ABSTRACT

A method and associated apparatus combine a calculation of chaos of a quantifiable cardiac characteristic associated with a patient with a measurement of a non-increasing parasympathetic activity of the patient to detect a physiological abnormality of the patient.

41 Claims, 8 Drawing Sheets

(51) Int. Cl.
A61B 5/11 (2006.01)
G06K 9/00 (2006.01)

(56) References Cited

U.S. PATENT DOCUMENTS

| | | | |
|---|---|---|---|
| 7,711,415 B1 * | 5/2010 | Farazi | A61B 5/0245 600/509 |
| 2009/0105601 A1 * | 4/2009 | Kamata | A61B 5/02405 600/515 |
| 2011/0224517 A1 | 9/2011 | González et al. | |
| 2011/0270095 A1 * | 11/2011 | Bukhman | A61B 5/0452 600/483 |
| 2011/0306845 A1 | 12/2011 | Osorio | |

OTHER PUBLICATIONS

Abboud; "In Search of Autonomic Balance: The Good, The Bad, and The Ugly;" American Journal Regul Integr Comp Physical 298; Mar. 10, 2010; pp. 1449-1467.
Aljadeff et al.; "Heart Rate Variability in Children with Obstructive Sleep Apnea;" 1997 American Sleep Disorders Association and Sleep Research Society; Sleep 20(2); Nov. 1996; pp. 151-157.
Arzeno et al.; Analysis of First-Derivative Based QRS Detection Algorithms; IEEE Transactions on Biomedical Engineering; vol. 55, No. 2; Feb. 2008; pp. 478-484.
American Thoracic Society; "Standards and Indications for Cardiopulmonary Sleep Studies in Children;" American Journal of Respiratory and Critical Care Medicine; vol. 153; Apr. 1996; pp. 866-878
Baharav et al.; "Autonomic Cardiovascular Control in Children with Obstructive Sleep Apnea;" Clinical Autonomic Research; vol. 9; Dec. 1999; pp. 345-351.
Barahona et al.; "Detection of Nonlinear Dynamics in Short, Noisy Time Series;" Letters to Nature; vol. 381; May 16, 1996; pp. 215-217.
Berntson et al.; "Heart Rate Variability: Origins, Methods, and Interpretive Caveats;" Psychophysiology; vol. 34, Issue 6; Nov. 1997; pp. 623-648.
Burr; "Interpretation of Normalized Spectral Heart Rate Variability Indices in Sleep Research: A Critical Review;" Sleep, vol. 30, No. 7, Jul. 2007; pp. 913-919.
Chaicham et al.; "Model-Based Assessment of Cardiovascular Autonomic Control in Children with Obstructive Sleep Apnea;" Daytime Autonomic Function in Pediatric OSA; Sleep, vol. 32, No. 7; Jul. 2009; pp. 927-938.
Deng et al.; "Heart Rate Variability in Pediatric Obstructive Sleep Apnea;" IEEE Proceedings of the 28$^{th}$ EMBS Annual International Conference; Aug. 2006; pp. 3565-3567.
Fitzmaurice et al; "Generalized Linear Mixed Effects Models: Approximate Methods of Estimation;" Applied Longitudinal Analysis; Wiley Series in Probability and Statistics; Book, Copyright 2011; 2 sheets.
Gaultier; "Cardiorespiratory Adaptation During Sleep in Infants and Chlidren;" Pediatric Pulmonology; vol. 19; Feb. 1995; pp. 105-117.
Goh et al.; "Sleep Architecture and Respiratory Disturbances in Children with Obstructive Sleep Apnea;" American Journal of Respiratory and Critical Care Medicine; vol. 162; Aug. 2000; pp. 682-686.
Gozal et al; "New Approaches to the Diagnosis of Sleep-Disordered Breathing in Children;" Elsevier: Sleep Medicine; vol. 11, Issue 7; Aug. 2010; pp. 708-713.
Hopf et al.; "Low-frequency Spectral Power of Heart Rate Variability is Not a Specific Marker of Cardiac Sympathetic Modulation;" Clinical Investigations; Anesthesiology; vol. 82, No. 3; Mar. 1995; pp. 609-610.
Houle et al.; "Low-frequency Component of the Heart Rate Variability Spectrum: A Poor Marker of Sympathetic Activity;" The American Physiological Society; vol. 276, No. 1; Jan. 1999; pp. H215-H223.
Katz et al.; "Diagnosis of Obstructive Sleep Apnea Syndrome in Infants and Children;" Principles and Practice of Pediatric Sleep Medicine; Apr. 2005; pp. 197-210.
Katz et al.; "Night-to-night Variability of Polysomnography in Children with Suspected Obstructive Sleep Apnea;" Journal of Pediatrics; vol. 140, Issue 5; May 2002; pp. 589-594.
Katz et al.; "Pulse Transit Time as a Measure of Arousal and Respiratory Effort in Children with Sleep-Disordered Breathing;" Pediatric Research; vol. 53, No. 4; Jan. 2003; pp. 580-588.
Katz et al.; "Genioglossus Activity During Sleep in Normal Control Subjects and Children with Obstructive Sleep Apnea;" American Journal of Respiratory and Critical Care Medicine; vol. 170; Sep. 2004; pp. 533-560.
Katz et al.; "Pathophysiology of Pediatric Obstructive Sleep Apnea;" Proceedings of the American Thoracic Society: vol. 5, No. 1; Feb. 2008; pp. 253-262.
Katz et al.; "Pediatric Obstructive Sleep Apnea Syndrome;" Clinical Chest Medicine; vol. 31; Jan. 2010; pp. 221-234.
Kheirandish-Gozal et al.; "Autonomic Alterations and Endothelial Dysfunction in Pediatric Obstructive Sleep Apnea;" Sleep Medicine; vol. 11; Aug. 2010; pp. 714-720.
Leuenberger et al.; "Surges of Muscle Sympathetic Nerve Activity During Obstructive Apnea are Linked to Hypoxemia;" Journal of Applied Physiology; Aug. 1995; pp. 581-588.
Lioa et al.; "Sleep-disordered Breathing in Children is Associated with Impairment of Sleep Stage Specific Shift of Cardiac Autonomic Modulation;" Journal of Sleep Research; vol. 19; Mar. 2010; pp. 358-365.
Liao et al.; "Sleep-disordered Breathing and and Cardiac Autonomic Modulation in Children;" Sleep Medicine; vol. 11; May 2010; pp. 484-488.
Marcus; "Sleep-disordered Breathing in Children;" American Journal of Respiratory and Critical Care Medicine; vol. 164; Jul. 2001; pp. 866-878.
Martin et al.; "Wigner-Ville Spectral Analysis of Nonstationary Processes;" IEEE Transactions on Acoustics, Speech, and Signal Processing. vol. ASSP-31, No. 6; Dec. 1985; pp. 1461-1470.
Notarius et al.; "Dissociation mnBetween Microneurographic and Heart Rate Variability Estimates of Sympathetic Tone in Normal Subjects and Patients with Heart Failure;" Clinical Science; vol. 96; Jan. 1999; pp. 557-656.
Poon et al.; "Decrease of Cardiac Chaos in Congestive Heart Failure;" Letters to Nature; vol. 389; Oct. 1997; pp. 492-495.
Poon et al.; "Titration of Chaos with Added Noise;" Proceedings of the National Academy of Sciences; vol. 98, No. 13; Jun. 2001; pp. 7107-7112.
Poon et al.; "A Unified Theory of Chaos Linking Noniinear Dynamics and Statistical Physics;" Cornell University Library; Apr. 2010; pp. 1-13.
Shouldice et al.; "Detection of Obstructive Sleep Apnea in Pediatric Subjects Using Surface Lead Electrocardiogram Features;" Sleep; vol. 27. No. 4; Jan. 2004; pp. 784-792.
Smith et al.; "Role of Hypoxemia in Sleep Apnea-Induced Sympathoexcitation;" Journal of the Autonomic Nervous System; vol. 56; Jan. 1996; pp. 184-190.
Snyder et al.; "Changes in Respiration, Heart Rate, and Systolic Blood Pressure in Human Sleep;" Journal of Applied Physiology; vol. 19, No. 3; May 1964; pp. 417-422
Somers et al.; "Sympathetic-Nerve Activity During Sleep in Normal Subjects;" New England Journal of Medicine; vol. 328; No. 5; Feb. 1993; pp. 303-307.
Somers et al.; "Sympathetic Neural Mechanisms in Obstructive Sleep Apnea;" Journal of Clinical Investigation; vol. 96; Oct. 1996; pp. 1897-1904.
Sugihara et al.; "Nonlinear Control of Heart Rate Variability in Human Infants;" Proceedings of the National Academy of Sciences; vol. 93; Mar. 1996; pp. 2608-2613.
"Heart Rate Variability; Standards of Measurement, Physiological Interpretation, and Clinical Use;" Task Force of the European Society of Cardiology of the North American Society of Pacing Electrophysiology; vol. 93; Jan. 1996; pp. 1043-1065.

(56) References Cited

OTHER PUBLICATIONS

Wu et al; "Chaotic Signatures of Heart Rate Variability and Its Power Spectrum in Health, Aging and Heart Failure;" PLoS ONE; vol. 4, Issue 2; e4323; Feb. 2009; pp. 1-9.
Yaggi et al.; Adult Obstructive Sleep Apnea/Hypopnea Syndrome: Definitions, Risk Factors; and Pathogenesis; Clinical Chest Medicine; vol. 31; Issue 2; Jan. 2010; pp. 179-186.
Zapanta et al.; "Heart Rate Chaos in Obstructive Sleep Apnea in Children;" Proceedings of the $26^{th}$ Annual International Conference of the IEEE Engineering in Medicine and Biology Magazine; Sep. 2004; pp. 3889-390.
PCT International Preliminary Report on Patentability and Written Opinion of the ISA Dated Aug. 13, 2015; For PCT Pat. App. No. PCT/US2013/075577; 9 Pages.

\* cited by examiner

SYSTEMS AND METHODS FOR DETECTING A PHYSIOLOGICAL ABNORMALITY IN A PATIENT BY USING CARDIAC OR OTHER CHAOS IN COMBINATION WITH NON-INCREASING PARASYMPATHETIC MODULATION

STATEMENT REGARDING FEDERALLY SPONSORED RESEARCH

This invention was made with Government support under Grant Nos. R01 HL067966, R01 HL079503, R21 HL075014, and RC1 RR028241 awarded by the National Institutes of Health. The Government has certain rights in the invention.

FIELD OF THE INVENTION

This invention relates generally to detection of physiological abnormalities and, more particularly, to systems and methods that use chaos of a measured parameter associated with a patient's heart function or other function in combination with a measurement of a non-increasing parasympathetic activity of the patient to detect the physiological abnormalities.

BACKGROUND OF THE INVENTION

Chaos exhibited, for example, in a sequence of numerical values, can be described in a variety of ways. Simply stated, chaos in a sequence of numbers is indicative of the sequence of numbers that is at least initially deterministic, but that is complex and that displays apparent random characteristics and becomes unpredictable in a long term. Generally, a chaotic system and/or a chaotic model are nonlinear and very sensitive to initial input conditions. Chaos is more fully described below.

It has been recognized that electrical signals produced by a human heart reflect activity of a nonlinear dynamical system, which may be described using chaos theory. Chaos in general and chaos of electrical signals produced by the heart have been described, for example, in U.S. Pat. No. 5,792,062, issued Aug. 11, 1998, and in U.S. Pat. No. 5,938,594, issued Aug. 17, 1999, both of which are incorporated by reference herein in their entireties, and both of which are assigned to the assignee of the present invention.

Accordingly, the human heart may be referred to as nonlinear dynamical or chaotic system. Dynamical systems, such as the heart, can exhibit both periodic and chaotic behavior depending upon certain system parameters. These parameters appear as constants in mathematical equations describing the heart system. However, the chaotic behavior exhibited by the heart is not immediately obvious when looking, for example, at an electrocardiograph (ECG) signal.

One way to observe the chaotic behavior of the heart is to plot interbeat spacing (i.e., heart interbeat interval) or its reciprocal (i.e., heart rate) at a time n against the interbeat spacing (or heart rate) at time n+1. Such a plot is referred to as a Poincare map or a return map. However, one problem with this technique is that a relatively large amount of data is required to provide an accurate representation of the heart system.

In general, problems arise in collecting large amounts of data from biosystems. For example, collection of a relatively large amount of bioelectric data on a human heart requires a human to wear a monitor or sensor for a relatively long period of time. Moreover, relatively large processing power is required to analyze the large amount of data retrieved from the human subject or other biosystem. The need to process such large amounts of data makes it relatively difficult to provide a real time processing system. Furthermore, a relatively large amount of storage capacity is required to store the large amount of collected data. Most importantly, analyses that require large amounts of data collected over a protracted period are susceptible to time-dependent changes in the system states that may occur during the data collection period, hence such analyses cannot detect any rapid changes in systems states.

Chaotic behavior of the heart can be linked to sympathetic or to parasympathetic behavior of the autonomic nervous system.

It is known that many diseases such as sleep apnea and heart failure present with increased sympathetic behavior. However, detection of sympathetic behavior has been difficult and invasive techniques have been used.

Attempts have been made to detect physiological abnormalities by measuring variations of a quantifiable characteristic of a patient's heart. For example, attempts have been made to detect sleep apnea by measuring a high frequency portion and/or a low frequency portion of a power spectrum of a heart rate and/or of a heart interbeat interval of a patient.

However, the high frequency portion of the power spectrum is linked to parasympathetic behavior of the autonomic nervous system and is not a direct indicator of sympathetic behavior in itself. Evidence of the relationship between the high frequency portion of the power spectrum and parasympathetic behavior can be seen in clinical and experimental observations of autonomic maneuvers such as vagus nerve stimulation, muscarinic receptor blockage, and vagotomy, for which the efferent vagal activity is a major contributor to the high frequency portion of the heart rate or interbeat interval power spectrum.

The low frequency portion of the power spectrum appears to reflect both sympathetic and parasympathetic activity and therefore, is also not a good indicator of sympathetic activity.

It would be desirable to provide a method and apparatus to detect physiological abnormalities by measuring variations of a quantifiable characteristic of a heart of a patient, where the quantifiable characteristic is linked to sympathetic behavior of the autonomic nervous system. It would be desirable to provide such a method and apparatus that have high sensitivity and high specificity in detecting the physiological abnormality. In other words, it would be desirable to provide such a method and apparatus that can detect even mild amounts of the physiological abnormality and with a low rate of false detections. It would be desirable to provide such a method and apparatus that are non-invasive. It would be desirable to provide such a method and apparatus that are robust, namely, that have an ability to reject artifacts, like disturbances and noise.

SUMMARY OF THE INVENTION

The present invention provides a method and apparatus to detect physiological abnormalities by measuring variations of a quantifiable characteristic of a heart of a patient, where the quantifiable characteristic is linked to sympathetic behavior of the autonomic nervous system. The present invention provides such a method and apparatus that have high sensitivity and high specificity in detecting the physiological abnormality. In other words, the present invention provides such a method and apparatus that can detect even mild amounts of the physiological abnormality and with a low rate of false detections. The present invention provides such a method and apparatus that are non-invasive. The present invention also provides such a method and apparatus that are robust, namely, that have an ability to reject artifacts, like disturbances and noise In accordance with one aspect of the present invention, a method of detecting a physiological abnormality includes measuring a quantifiable characteristic of a patient. The method also includes quantifying, with a processor, a chaos of the quantifiable characteristic. The method also includes identifying, with the processor, a non-increasing parasympathetic activity in the patient. The method also includes combining, with the processor, the quantified chaos and the identified non-increasing parasympathetic activity to determine that the chaos is a result of sympathetic activity in the patient. The method also includes detecting, with the processor, the physiological abnormality in accordance with the combining.

In accordance with another aspect of the present invention, a system to detect a physiological abnormality includes a patient sensor coupled to a patient and configured to measure a quantifiable characteristic of the patient. The system also includes a processor configured to: quantify a chaos of the quantifiable characteristic; identify a non-increasing parasympathetic activity in the patient; combine the quantified chaos and the identified non-increasing parasympathetic activity to determine that the chaos is a result of sympathetic activity in the patient; and detect the physiological abnormality in accordance with the combining.

In accordance with another aspect of the present invention, a non-transitory computer readable storage medium comprising instructions for detecting a physiological abnormality, the instructions comprising instructions for: measuring a quantifiable characteristic of a patient; quantifying a chaos of the quantifiable characteristic; identifying a non-increasing parasympathetic activity in the patient; combining the quantified chaos and the identified non-increasing parasympathetic activity to determine that the chaos is a result of sympathetic activity in the patient; and detecting the physiological abnormality in accordance with the combining.

BRIEF DESCRIPTION OF THE DRAWINGS

The foregoing features of the invention, as well as the invention itself may be more fully understood from the following detailed description of the drawings, in which.

DETAILED DESCRIPTION OF THE INVENTION

Figure 1:
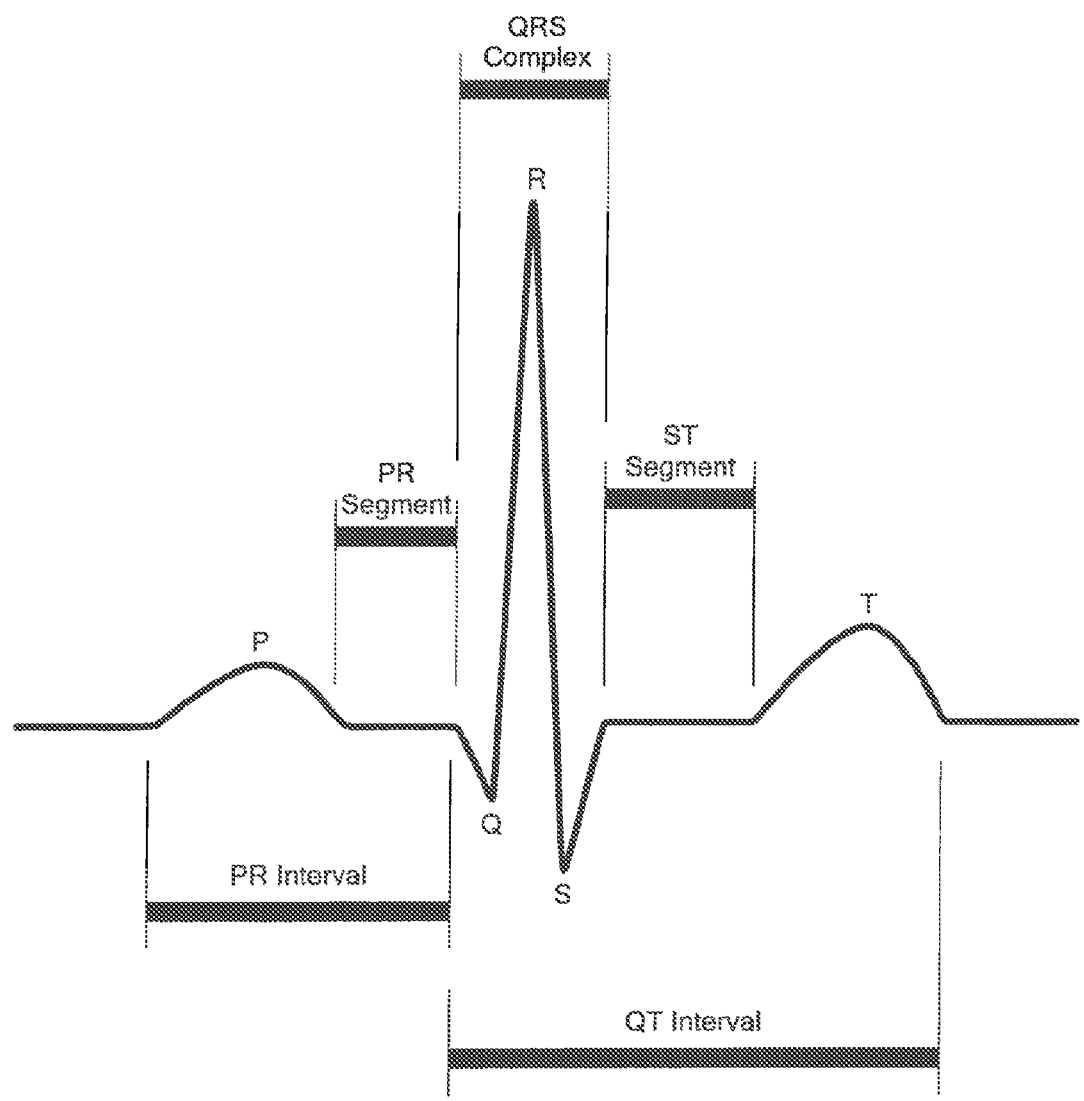
FIG. 1 is a graph showing a heartbeat of a person as measured electrically by an electrocardiogram (EKG) system.

Before describing the present invention, some introductory concepts and terminology are explained. As used herein, the term "noise titration" is used to describe a numerical method described in above-mentioned U.S. Pat. No. 5,792,062 and U.S. Pat. No. 5,938,594, which method can identify a relative amount of chaos in a sequence of values. Simply stated, an amount of non-linearity is first measured in a sequence of values. If non-linearity can be measured in the sequence of values, an increasing amount of random noise is added to the sequence of numbers until a noise limit (NL) is reached, beyond which point, the non-linearity can no longer be detected. The noise limit (NL) is related in a relative sense to an amount of chaos in the original sequence of values. The noise titration technique is further described below in conjunction with FIGS. 6 and 6A.

Traditionally, so-called "deterministic chaos" is defined as a form of low-dimensional nonlinear dynamics with bounded trajectories in the state space that exhibit sensitive dependence on initial conditions, such that the trajectories are relatively predictable in the short term but become increasingly unpredictable in the long term. This behavior is distinct from classical forms of nonlinear dynamics such as stable (or unstable) equilibrium points where the trajectories eventually converge to (or diverge from) a fixed point, or stable (or unstable) limit cycles where the trajectories converge to (or diverge from) a periodic orbit. Unlike these classical forms of nonlinear dynamics, the trajectories of deterministic chaos never converge to a fixed point or periodic orbit, hence cannot be predicted in the long run, although they remain bounded and never diverge to infinity.

One factor that makes deterministic chaos interesting and useful is that the underlying processes can be analyzed using low-dimensional dynamical models. In contrast, processes that exhibit high-dimensional nonlinear dynamics have been traditionally considered as "noise" because they are mathematically and computationally intractable and cannot be analyzed by means of deterministic models. In the field of statistical physics, noise models are analyzed probabilistically using stochastic theory for random processes.

Deterministic chaos is a mathematical construct that tends to exist only in theory. In practice, deterministic chaos processes are difficult to observe because any observation is necessarily distorted by measurement noise or measurement error. In fact, deterministic chaos cannot be simulated because of the finite precision of analog or digital computation. This is the nonlinear dynamics equivalent of the "Uncertainty Principle" in quantum mechanics. The above-described noise titration technique circumvents the problem of measurement noise by assessing changes in deterministic chaos when observed under the influence of measurement noise or inaccuracy. The 'noise limit' index, NL, provides a relative measure of chaos strength.

Deterministic chaos and other low-dimensional nonlinear dynamical processes rarely exist in isolation and may be constantly perturbed by high-dimensional processes or random noise (called 'dynamic noise', to distinguish it from measurement noise) that interact with them.

So-called "noise-induced chaos" can be described in a different way. Namely, when perturbed by dynamic noise of suitable intensity, a low-dimensional nonlinear dynamical process may exhibit chaos-like complex trajectories with short-term predictability and long-term unpredictability even though the process itself may not necessarily exhibit deterministic chaos in the absence of dynamic noise. Like deterministic chaos, changes in noise-induced chaos can also be detected by the noise titration technique. The two types of chaos may not be distinguishable under noise titration. Nevertheless, the detection of chaos (whether deterministic or noise-induced) by noise titration indicates the presence of low-dimensional nonlinear dynamics that can be modeled and analyzed deterministically apart from possible disturbances from measurement and dynamic noise.

The noise titration technique (or any other chaos detection technique) is limited by the signal-to-noise ratio of the data. When the measurement noise or dynamic noise becomes so strong that it exceeds the 'noise floor' for the data, then the underlying low-dimensional nonlinear dynamics can no longer be detected. This is called noise annihilation of chaos. A sensitive chaos detection technique may detect the low-dimensional nonlinear dynamics even in the presence of strong measurement noise and dynamic noise. The noise titration technique is a sensitive method for chaos detection.

In view of the above, as used herein, the term "chaos" includes both deterministic chaos and noise-induced chaos.

For a more extensive discussion of chaos, see, e.g., Chi-Sang Poon, Cheng Li, and Guo-Qiang Wu, "A unified theory of chaos linking nonlinear dynamics and statistical physics," ARXIV10041427, 2010, which publication is incorporated by reference herein in its entirety.

It should be understood that the above-described noise titration technique is but one method that can be used to detect chaos, and the discussions herein below regarding detection of chaos can include other methods to detect chaos, be it deterministic or noise-induced.

Sleep apnea is described herein as an example of a physiological abnormality that can be identified by way of detection of quantifiable characteristics of the heart. However, other physiological abnormalities can also be identified, for example, heart failure.

Obstructive sleep apnea syndrome (OSAS) is characterized by intermittent episodes of disrupted breathing due to pharyngeal narrowing or collapse, resulting in hypoxemia, hypercapnia, and/or sleep disruption. OSAS reportedly affects at least two percent of children in the United States and in Europe, though about ten percent habitually snore. The etiology and clinical manifestations of OSAS in children are quite different from adults. In particular, children with OSAS may have normal sleep stage distribution, few electrocortical arousals, and obstructive events occurring predominantly during rapid eye movement (REM) sleep.

Airflow obstruction and REM sleep may both exert profound influences on autonomic regulation. Sympathetic nerve activity typically increases during REM sleep and with OSAS in adults. These effects are accompanied by concurrent parasympathetic withdrawal as identified from power spectrum analysis of heart rate variability (HRV). It has been reported that the HRV power spectrum in children has a significantly decreased high-frequency (HF) component and increased low-frequency to high-frequency power ratio (LF/HF) during rapid eye movement (REM) sleep as compared to non-REM (NREM) sleep and with moderate/severe OSAS compared to normal controls, indicating downregulation of parasympathetic activity in these conditions. However, since the LF power and LF/HF power ratio are nonspecific indicators of sympathetic outflow (which is a major drawback of conventional HRV analyses), it remains uncertain whether sympathetic activity is upregulated in children during REM sleep or with mild OSAS. A noninvasive method with high sensitivity and specificity in detecting even mild OSAS and associated autonomic abnormalities is critical in developing an effective home screening test for sleep apnea and for other physiological abnormalities, without the need for invasive recording of sympathetic nerve activity in children.

Another approach to assess cardiac-autonomic modulation of HRV is based on methods of nonlinear time series analysis. Nonlinear HRV can be demonstrated in infants. The above-described noise titration assay of nonlinear dynamics has shown that HRV in healthy young and elderly subjects has distinct chaotic signatures. In particular, the HRV chaos has been shown to exhibit a circadian rhythm. (see, e.g., Wu G Q, Arzeno N M, Shen L L, Tang D K, Zheng, D A, Zhao N Q, Eckberg D L, Poon C S (2009), "Chaotic signatures of heart rate variability and its power spectrum in health, aging and heart failure," PLoS ONE 4: e4323, which article is incorporated herein in its entirety).

The above-described noise limit, NL, can be correlated positively with the HF component of the HRV power spectrum and negatively with the ratio of LF/HF, particularly during nighttime (i.e., HF chaos). However, as described more fully below, a form of heart rate chaos referred to herein as "non-HF chaos," described more fully below, provides a more robust measure of changing cardiac sympathetic-parasympathetic activities than is possible with conventional HRV metrics, with sensitivity and specificity sufficient to detect even mild OSAS in children.

Referring to FIG. 1, a graph has a horizontal axis (not shown) with a scale an arbitrary units of time and a vertical axis (not shown) with a scale in arbitrary units of volts. An electrical signal is representative of an electrical measurement, as made by an electrocardiogram system, which is representative of a heartbeat of a human. Conventional nomenclature describes P, Q, R, S, and T portions (i.e., voltage values) of the electrical signal, and also, a PR interval having PR interval voltage and time values, a PR segment having PR segment voltage and time values, a QRS complex having QRS complex voltage and time values, a QT interval having QT interval voltage and time values, and an ST segment having ST segment voltage and time values. Absolute and relative characteristics of the voltage and time values can be used to diagnose normal or abnormal conditions of the heartbeat.

Figure 1A:
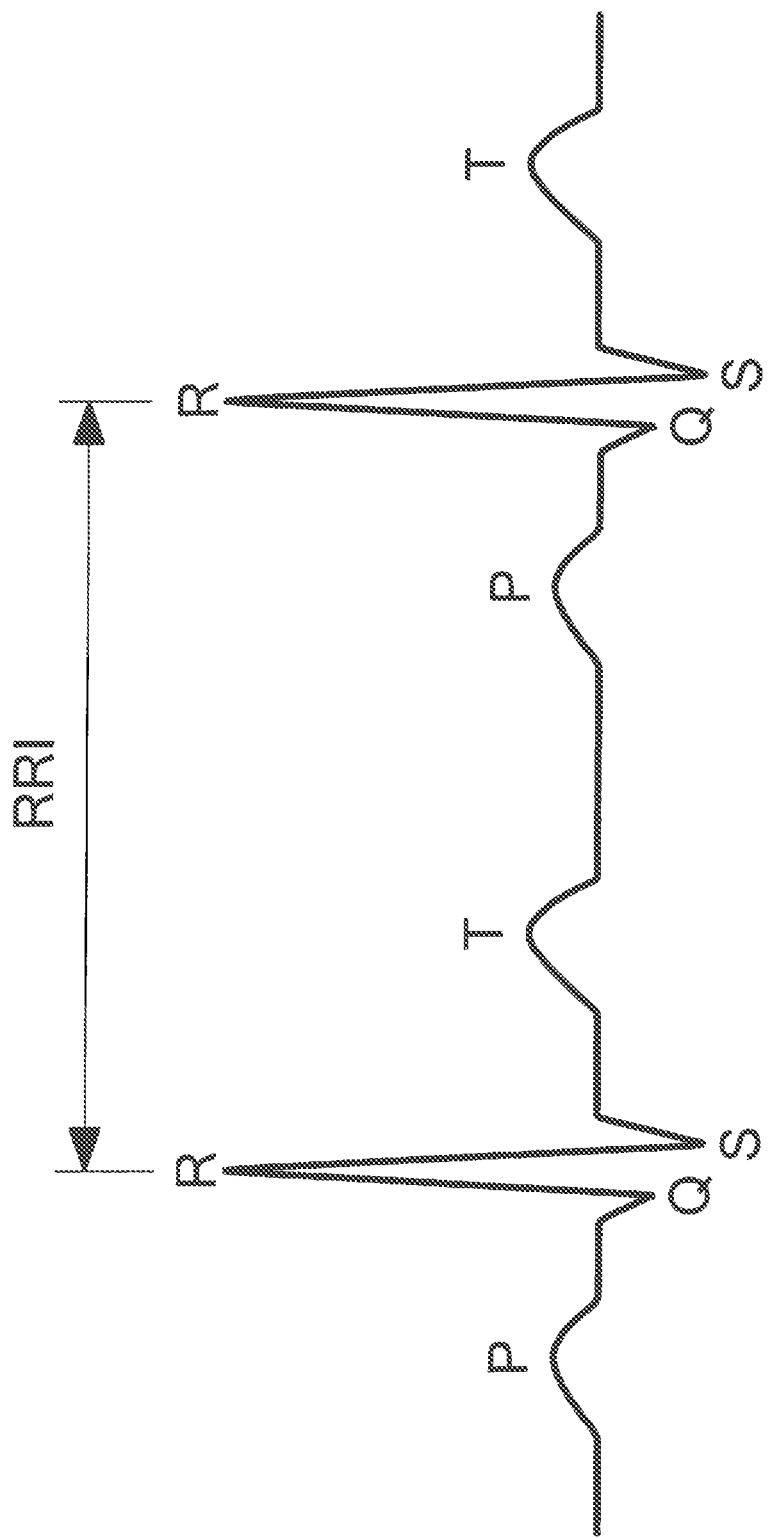
FIG. 1A is a graph showing a plurality of heart beats of a person as measured electrically by an EKG system.

Referring now to FIG. 1A, a graph shows electrical waveforms representative of an electrical measurement, as made by an electrocardiogram system, which is representative of a plurality of heart beats of a human. An R to R interval (RRI), also referred to herein as a "heart interbeat interval," is a time period between adjacent R values (i.e., peak values) of the QRS portion of the electrically measured heart beats. Thus, it will be appreciated that a sequence of values can be constructed, each indicative of a heart interbeat interval.

It will be understood that a heart rate value (units of heart beats per time) is a reciprocal of a heart interbeat interval value (units of time). The heart rate can be an instantaneous heart rate generated as a reciprocal of an instantaneous heart interbeat interval, or it can be a reciprocal of an average of several heart interbeat intervals. Thus, it will be appreciated that a sequence of values can be constructed, each value indicative of a heart rate.

As used herein, the term "heart rate variability" (HRV) is used to describe either a variability of heart interbeat interval or a variability of heart rate.

Many physiological abnormalities can be identified by way of irregularities of quantifiable characteristics associated with the heart, of which heart interbeat intervals and heart rate are but two of the quantifiable characteristics. However, other quantifiable characteristics associated with a patient can include, but are not limited to, blood oxygenation variability, blood pressure variability, respiratory ventilation variability, and respiratory rate (or interval) variability.

Figure 2:
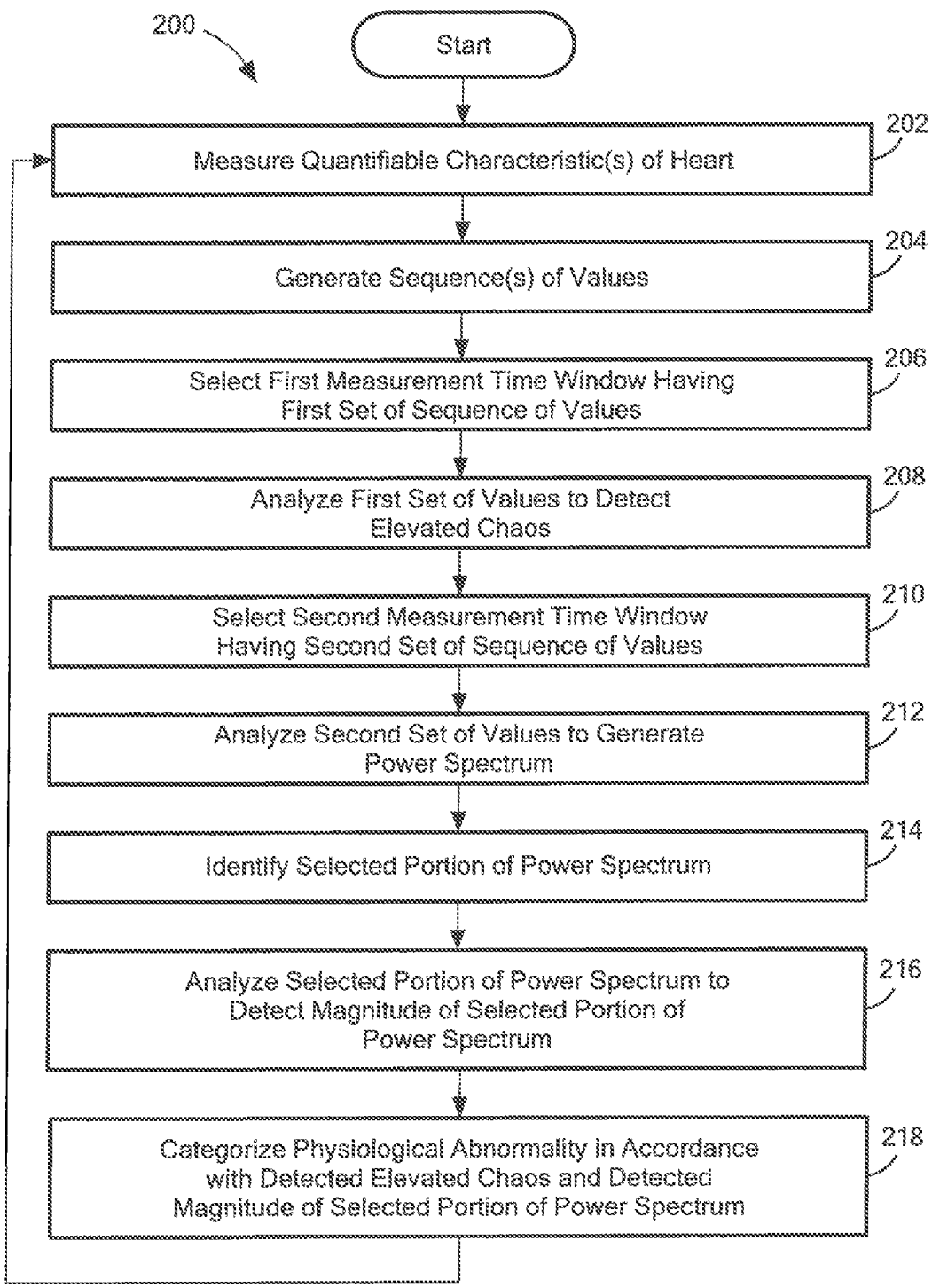
FIG. 2 is a flow chart showing a process that can be used to detect an abnormal physiological condition, e.g., sleep apnea, in a patient.
Figure 3:
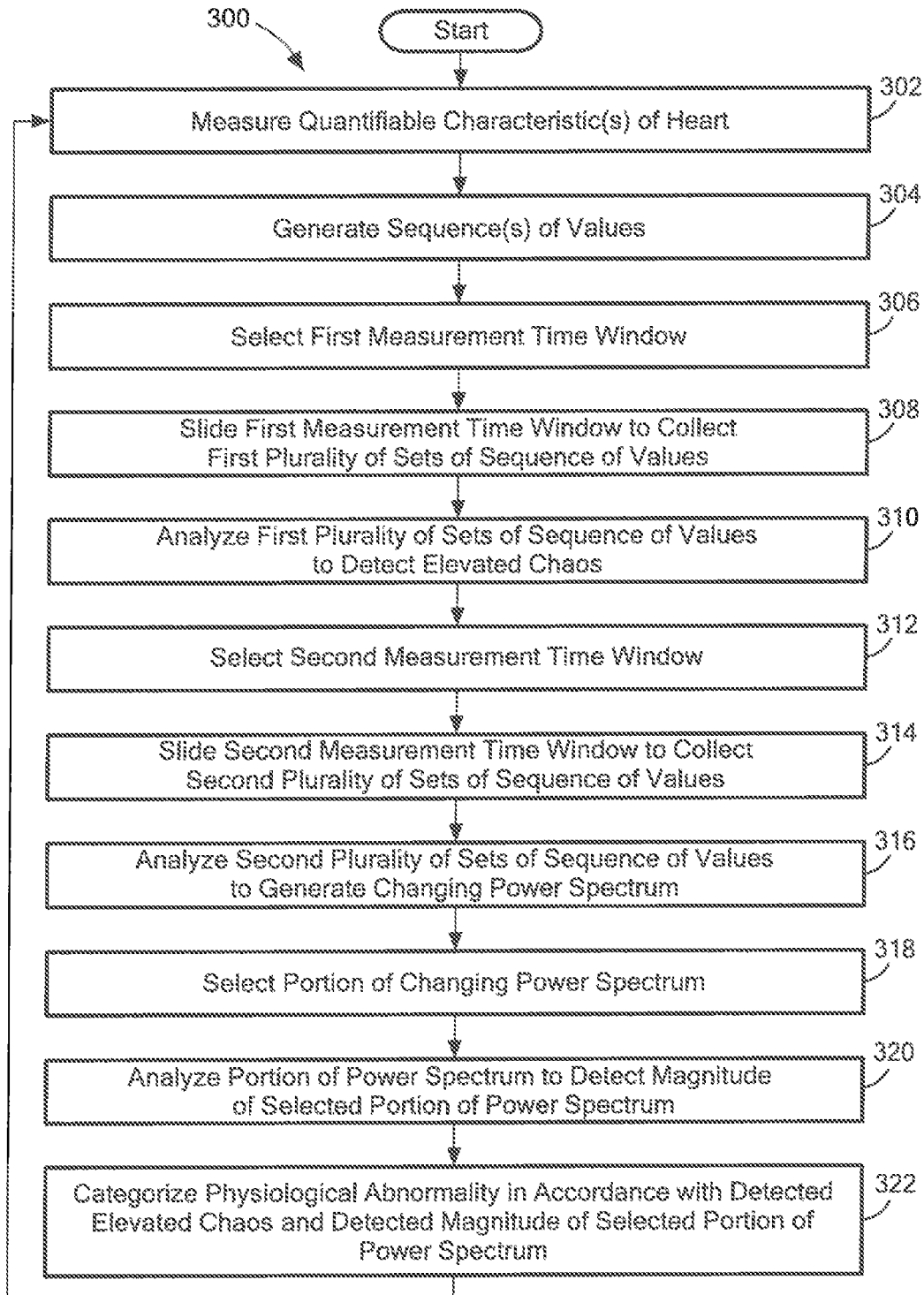
FIG. 3 is a flow chart showing another process that can be used to detect an abnormal physiological condition, e.g., sleep apnea, in a patient.
Figure 4:
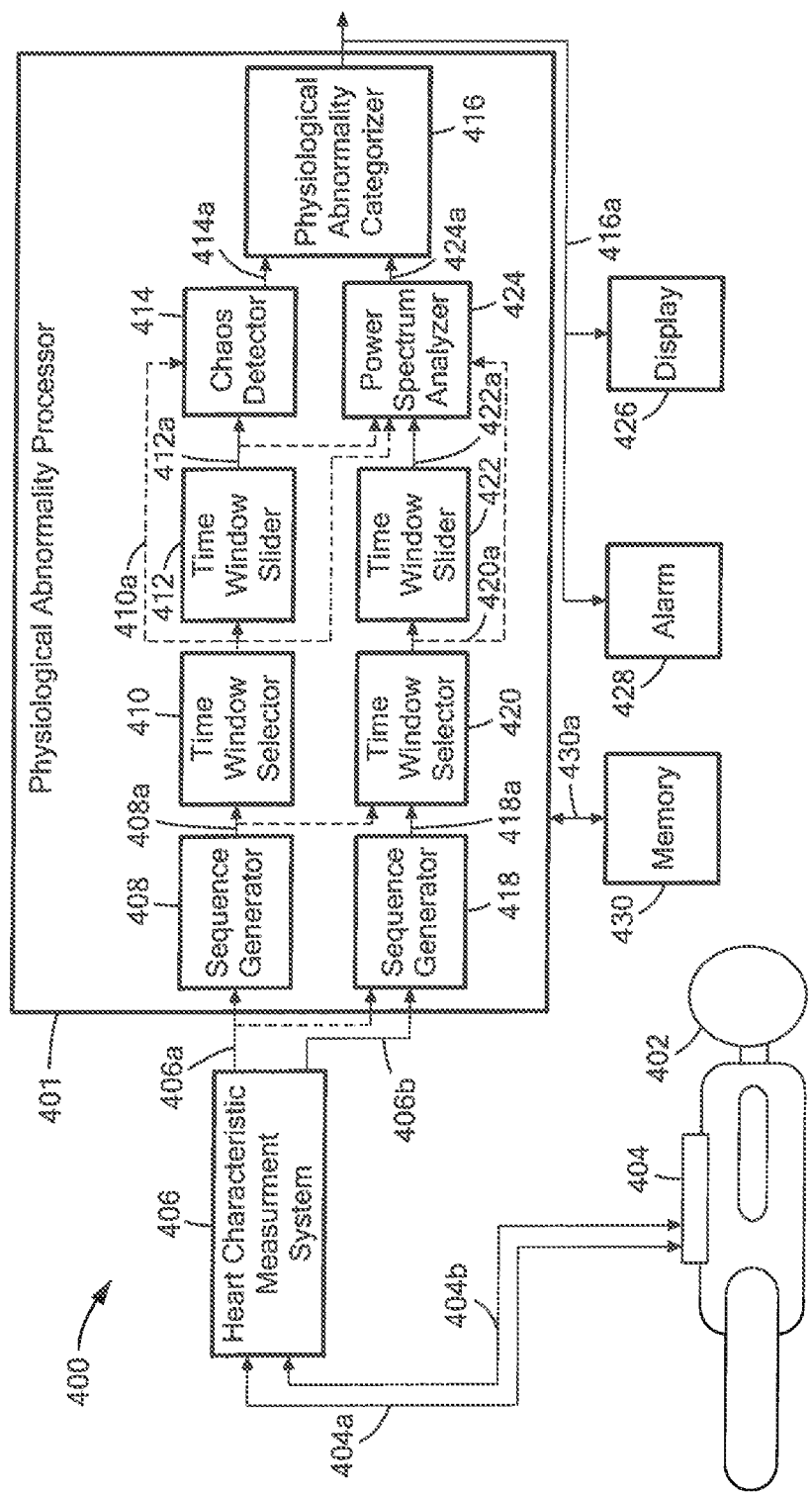
FIG. 4 is a block diagram showing a system that can be used to detect an abnormal physiological condition, e.g., sleep apnea, in a patient.

It should be appreciated that FIGS. 2 and 3 show flowcharts corresponding to the below contemplated technique which would be implemented in a computer system 401 (FIG. 4). Rectangular elements (typified by element 202 in FIG. 2), herein denoted "processing blocks," represent computer software instructions or groups of instructions. Diamond shaped elements (not shown), herein denoted "decision blocks," represent computer software instructions, or groups of instructions, which affect the execution of the computer software instructions represented by the processing blocks.

Alternatively, the processing and decision blocks represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required of the particular apparatus. It should be noted that many routine program elements, such as initialization of loops and variables and the use of temporary variables are not shown. It will be appreciated by those of ordinary skill in the art that unless otherwise indicated herein, the particular sequence of blocks described is illustrative only and can be varied without departing from the spirit of the invention. Thus, unless otherwise stated the blocks described below are unordered meaning that, when possible, the steps can be performed in any convenient or desirable order.

FIGS. 2 and 3 below show similar methods that can use a combination of a measurement of chaos associated with HRV, i.e., chaos of measured heart rate values or measured heart interbeat interval values, with another measurement of a quantifiable characteristic of the heart. For example, the other quantifiable characteristic can be representative of a magnitude of a high frequency portion of a power spectrum of the HRV, i.e., of the measured heart rate values or of the measured heart interbeat interval values.

It will be recognized from the above that an absence of an increase, or a decrease, of the high frequency portion of the power spectrum of the HRV is indicative of a non-increasing parasympathetic behavior. While the chaos alone may be indicative of either sympathetic or parasympathetic activity, if chaos of HRV (or chaos of a different measured parameter) occurs at the same time as the detected non-increasing parasympathetic behavior, it can be concluded that the chaos of the HRV is associated with sympathetic behavior, and is indicative of a physiological abnormality of the patient.

The presence of HRV chaos in combination with lack of increase, or decrease, of the high frequency portion of the power spectrum of the HRV is referred to herein as "non high frequency chaos" or "non-HF chaos." However, it should be understood that the presence of chaos in combination with any indicator of non-increasing parasympathetic activity can also be used as an indicator of sympathetic activity, and can also be used to detect a physiological abnormality.

Regarding the detection of sympathetic activity, techniques described herein are motivated by an observation that increase in non-high frequency HRV chaos, i.e., increase of chaos in combination with decrease or no change in HF power spectrum, is indicative of sympathoexcitation in sleep apnea. In the case of heart failure, the high frequency component of the power spectrum tends to be suppressed because of depression of parasympathetic activity. In this event, the magnitude of heartbeat chaos is also decreased because of the absence of high-frequency chaos (see, e.g., papers by Poon and Merrill, Nature 1997 and Wu et al., PLoS ONE, 2009). Even in these patients, the residual non-high frequency chaos is indicative of their heightened sympathetic activity.

While the high frequency portion of a power spectrum of the HRV is used to identify a non-increasing parasympathetic behavior in some embodiments described herein, in other embodiments, a different indicator of non-increasing parasympathetic behavior can be used. For example, blood oxygenation variability, blood pressure variability, respiratory ventilation variability, and respiratory rate (or interval) variability can be used to identify a non-increasing parasympathetic activity.

In some other embodiments, direct measurement of parasympathetic activity could instead be used to identify a non-increasing parasympathetic activity. However, direct measurement of parasympathetic activity is generally difficult. Parasympathetic activity can be directly measured by physiological response to vagus nerve stimulation (e.g. by Valsalva maneuva), or by response to blockade of certain receptors (e.g. $M_2$ receptors) via pharmacological agents (e.g. atropine or antimuscarinic). Other noninvasive approaches for assessing parasympathetic activity or suppression thereof include evaluation of heart rate variability as described above, heart rate recovery from exercise, and heart rate turbulence. Any of these techniques can be used to identify non-increasing parasympathetic activity. Thus, any of these direct measurement techniques can be combined with a measurement of chaos in order to indicate that the chaos is due to sympathetic activity and not due to parasympathetic activity.

While chaos of HRV is described herein, in other embodiments, the measurement of chaos, instead of using chaos of HRV, can use chaos of another quantifiable characteristic of or associated with a patient, for example, blood oxygenation variability, blood pressure variability, respiratory ventilation variability, and respiratory rate (or interval) variability.

Thus, while HRV is used in examples below, it will be understood that either the detection of chaos or the detection of non-increasing parasympathetic activity, or both, can use measurements of physiological parameters other than HRV, and also, chaos detection methods other than the noise titration technique can be used.

Referring now to FIG. 2, a method 200 begins at block 202, where one or more quantifiable characteristic of the heart are measured. The quantifiable characteristics can include, but are not limited to heart rate values or heart interbeat values (i.e., RRI values). In order to measure the heart rate values or heart interbeat values, the QRS peaks (i.e., R values) of the electrical signal of FIGS. 1 and 2 can be used.

Peak values, i.e., the R values, can be identified in a number of ways. For example, in some embodiments, the R peak values can be identified using a Hilbert transform-based peak extraction algorithm using samples of the EKG signal sampled, for example, with a sampling rate of about one hundred Hz. However, other sampling rates above or below one hundred HZ can also be used, and other peak detection algorithms can also be used. Also, other methods can be used to identify the peaks of the QRS portion of the electrical signals.

At block 204, one or more sequences of the measured values are generated. In some embodiments, a sequence of values corresponding to a series of heart interbeat intervals and/or or a sequence of values corresponding to a series of heart rate values is generated. However, in other embodiments, a different sequence of values representative of a different quantifiable characteristic associated with a patient can be generated, for example, blood oxygenation values, blood pressure values, respiratory ventilation, or respiration rate (or interval) values. In some embodiments, the respiration rate (or interval) values can be derived from an EKG signal.

In some embodiments, the sequence(s) of values generated at block 204 can have undesirable artifacts generated, for example, by movement of the patient. The artifact values can be removed from the sequence(s) of values. In some embodiments, the removed values are filled in with other values, for example, with an average value representative of an average of all of the remaining values in the respective sequence of values. However, in other embodiments, the removed values are merely removed and not replaced.

In some embodiments, the sequence(s) of values, with or without artifact removal, can be further manipulated. For example, in some embodiments for which the sequence of values is a time series, the time series can be converted to time series values that are equally spaced in time, for example, by using a cubic-spline interpolation with a sampling rate of about four Hz. However, other sampling rates can also be used.

At block 206, a first measurement time window, i.e., a so-called first "epoch," is selected. In some embodiments, the first epoch is about thirty seconds long. The first epoch can be associated with a first set of values within a first one of the sequences of values generated at block 204.

At block 208, the first set of values is analyzed, for example, with the above-described noise titration technique (further described in conjunction with FIGS. 6 and 6A), to detect a relative amount of chaos in the first set of values. It is determined if the relative amount of chaos has become elevated since a last set of values was analyzed. To this end, an upper chaos threshold can be used to identify if the chaos has increased. In some embodiments, a value of the upper chaos threshold is related to a long term average chaos value, i.e., and average NL value.

At block 210, a second measurement time window, i.e., a second epoch, is selected. In some embodiments, the second measurement time window is the same as the first measurement time window, i.e., the first and second epochs are the same, e.g., thirty seconds, and the same thirty seconds. However, in other embodiments, the first and second measurement time windows have different durations and may or may not overlap in time. The second epoch can be associated with a second set of values within a second one of the sequences of values.

In some embodiments, the second sequence of values and the second set of values therein can be the same as the first sequences of values and the first set of values therein. In some embodiments, the second sequence of values and the second set of values therein can be the same type of values as the first sequences of values and the first set of values therein, but taken at a different sampling rate. In some embodiments, the first and second time windows are the same and the first and second sets of values are the same. In some other embodiments, the first and second time windows are different in duration and the first and second sets of values are different.

However, in other embodiments, the second sequence of values and the second set of values therein can be different than the first sequences of values and the first set of values therein. For example, the first sequence of values and the first set of values therein can correspond to heart interbeat values and the second sequence of values and the second set of values therein can correspond to heart rate values. However, in other embodiments, the second set of values can be another quantifiable characteristic associated with a patient, for example, blood oxygenation values, blood pressure values, or respiration rate (or interval) values. As described above, in some embodiments, the respiration rate (or interval) values can be derived from an EKG signal. The other quantifiable characteristic of the heart can be selected to provide a measurement of parasympathetic behavior or lack thereof.

In some embodiments, the first measurement time window has a duration less than about five minutes and the second measurement time window has a duration less than about five minutes. However, in other embodiments, the first and second time windows can have durations of about one, two, five, ten, fifteen, twenty, twenty-five, thirty, sixty or one hundred twenty minutes.

At block 212, the second set of values is analyzed, for example, to generate a power spectrum from the second set of values.

At block 214, a portion of the power spectrum is selected. The portion of the power spectrum can be a portion within any selected frequency range. However, in other embodiments, the selected portion can be a portion within any selected amplitude range.

In some embodiments, the selected portion is a high frequency (HF) portion that spans a frequency range from about 0.15 Hz to about 0.4 Hz. In some other embodiments, the selected portion is a low frequency (LF) portion that spans a frequency range from about 0.04 Hz to about 0.15 Hz. However, other frequency ranges can be used for the low and high frequency portions.

At block 216, a magnitude or a power of the selected portion of the power spectrum is calculated and analyzed to determine if a relative magnitude or power has changed. In some alternate embodiments, instead, a ratio of LF and HF portions of the power spectrum is calculated and analyzed to determine if the ratio has changed.

At block 218, a physiological abnormality is identified in accordance with a detected elevated magnitude of the chaos calculated at block 208 and in accordance with the analysis of the selected portion of the power spectrum made at block 216.

In some embodiments, the physiological abnormality is detected in accordance with the elevated chaos and in accordance with a lack of change or a decrease in power of the HF portion of the power spectrum at the same time. To this end, an upper HF power threshold, and optionally also a lower HF power threshold, can be used to identify if the power of the HF portion of the power spectrum has remained relatively unchanged or has decreased. In some embodiments, values of the upper and lower HF power thresholds are related to a long term average HF power value.

In some other embodiments, the physiological abnormality is detected in accordance with the elevated chaos and in accordance with a decrease in power of the HF portion of the power spectrum at the same time. To this end, a lower HF power threshold can be used to identify if the power of the HF portion of the power spectrum has decreased. In some embodiments, a value of the lower HF power threshold is related to a long term average HF power value.

In some other embodiments, the physiological abnormality is detected in accordance with the elevated chaos and in accordance with a lack of change or an increase of a ratio of powers of the LF and HF portions of the power spectrum at the same time. To this end, an upper LF/HF ratio power threshold, and optionally, a lower LF/HF power threshold, can be used to identify if the ratio of the powers of LF and HF portions of the power spectrum has remained relatively unchanged or has increased. In some embodiments, values of the upper and lower LF and HF ratio power thresholds are related to a long term average LF/HF power ratio value.

In some other embodiments, the physiological abnormality is detected in accordance with the elevated chaos and in accordance with an increase in a ratio of powers of the LF and HF portions of the power spectrum at the same time. To this end, an upper LF/HF ratio power threshold can be used to identify if the ratio of the powers of LF and HF portions of the power spectrum has increased. In some embodiments, a value of the lower LF and HF ratio power threshold is related to a long term average LF/HF power ratio value.

The process 200 returns to block 202 where the quantifiable characteristic is again measured to generate one or more new sequences of values and the process repeats.

In some embodiments, the physiological abnormality is sleep apnea. In other embodiments, the physiological abnormality is chronic or acute heart failure. However, other physiological abnormalities may be detected with the methods described herein.

Referring now to FIG. 3, a process 300 is similar to the process 200 of FIG. 2, except the process 300 can use sliding sets of sequences of values and can process the sliding sets.

At block 302, one or more quantifiable characteristic of the heart are measured. The quantifiable characteristics can include, but are not limited to heart rate values or heart interbeat values (i.e., RRI values). As described above, in order to measure the heart rate values or heart interbeat values, the QRS peaks (i.e., R values) of the electrical signal of FIGS. 1 and 2 can be used.

At block 304, one or more sequences of the measured values are generated. In some embodiments, a sequence of values corresponding to a series of heart interbeat intervals and/or or a sequence of values corresponding to a series of heart rate values is generated. However, in other embodiments, a different sequence of values representative of a different quantifiable characteristic of or associated with a patient can be generated, for example, blood oxygenation values, blood pressure values, respiratory ventilation, or respiration rate (or interval) values. In some embodiments, the respiration rate (or interval) values can be derived from an EKG signal.

In some embodiments, the sequence(s) of values generated at block 304 can have undesirable artifacts generated, for example, by movement of the patient. The artifact values can be removed from the sequence(s) of values. In some embodiments, the removed values are filled in with other values, for example, with an average value representative of an average of all of the remaining values in the respective sequence of values. However, in other embodiments, the removed values are merely removed and not replaced.

In some embodiments, the sequence(s) of values, with or without artifact removal, can be further manipulated. For example, in some embodiments for which the sequence of values is a time series, the time series can be converted to time series values that are equally spaced in time, for example, by using a cubic-spline interpolation with a sampling rate of about four Hz. However, other sampling rates can also be used.

At block 306, a first measurement time window, i.e., a first epoch, is selected. In some embodiments, the first epoch is about thirty seconds long. The first epoch can be associated with a first plurality of sets set of values, each within a first sequence of values.

At block 308, the first time measurement window is slid in time to collect a first plurality of sets of values, each set of values within a respective epoch corresponding to a duration of the first epoch.

At block 310, the first plurality of sets of set values is analyzed, for example, with the above-described noise titration technique, to detect respective relative amounts of chaos in the first plurality of sets of values. It is determined if the amount of chaos has become elevated within the first plurality of sets of values.

At block 312, a second measurement time window, i.e., a second epoch, is selected. In some embodiments, the second measurement time window is the same as the first measurement time window, i.e., the first and second epochs are the same, e.g., thirty seconds, and the same thirty seconds. However, in other embodiments, the first and second measurement time windows have different durations. The second epoch can be associated with a second plurality of sets set of values, each within a second sequence of values.

In some embodiments, the second sequence of values and the second plurality of sets of values therein can be the same as the first sequences of values and the first plurality of sets of values therein. In some embodiments, the second sequence of values and the second set of values therein can be the same type of values as the first sequences of values and the first set of values therein, but taken at a different sampling rate. In some embodiments, the first and second time windows are the same and the first and second sets of values are the same. In some other embodiments, the first and second time windows are different in duration and the first and second sets of values are different.

However, in other embodiments, the second sequence of values and the second plurality of sets of values therein can be different that the first sequences of values and the first plurality of sets of values therein. For example, the first sequence of values and the first plurality of sets of values therein can correspond to heart interbeat values and the second sequence of values and the second plurality of sets of values therein can correspond to heart rate values. However, in other embodiments, the second plurality of sets of value can be another quantifiable characteristic associated with a patient, for example, blood oxygenation values, blood pressure values, respiratory ventilation or respiration rate (or interval) values. As described above, in some embodiments, the respiration rate (or interval) values can be derived from an EKG signal. The other quantifiable characteristic can be selected to provide a measurement of parasympathetic behavior or lack thereof.

In some embodiments, the first measurement time window has a duration less than about five minutes and the second measurement time window has a duration less than about five minutes. However, in other embodiments, the first and second time windows can have durations of about one, two, five, ten, fifteen, twenty, twenty-five, thirty, sixty or one hundred twenty minutes.

At block 314, the second time measurement window is slid in time to collect the second plurality of sets of values, each set of values within a respective epoch corresponding to a duration of the second epoch.

At block 316, the second plurality of sets of values is analyzed. For example, respective power spectra are generated from the second plurality of sets of values.

At block 318, a portion of the power spectra is selected. The portion of the power spectra can be a portion within any selected frequency range. However, in other embodiments, the selected portion can be a portion within any selected amplitude range.

In some embodiments, the selected portion is a high frequency (HF) portion that spans a frequency range from about 0.15 Hz to about 0.4 Hz. In some other embodiments, the selected portion is a low frequency (LF) portion that spans a frequency range from about 0.04 to about 0.15 Hz. However, other frequency ranges can be used for the low and high frequency portions.

At block 320, a magnitude or power of the selected portion of the power spectrum is calculated and analyzed to determine if the magnitude or power has changed. In some alternate embodiments, a ratio of the LF and HF portions is analyzed.

At block 322, a physiological abnormality is identified in accordance with a detected elevated magnitude of the chaos calculated at block 310 and in accordance with the analysis of the selected portion of the power spectra made at block 320.

Different analyses of the power spectrum described above in conjunction with FIG. 2 also pertain to the method 300 of FIG. 3.

The process 300 returns to block 302 where the quantifiable characteristic is again measured to generate one or more new sequences of values and the process repeats.

In some embodiments, the physiological abnormality is sleep apnea. In other embodiments, the physiological abnormality is sudden infant death syndrome (SIDS).

However, other physiological abnormalities may be detected with the methods described herein.

Referring now to FIG. 4, an apparatus 400 can be coupled to a patient 402, who can be lying, standing, or sitting.

The apparatus 400 can include one or more sensors 404 configured to generate one or more sensor signals, e.g., sensor signals 404a, 404b. A heart characteristic measurement system 406 is coupled to receive the sensor signals 404a, 404b and configured to generate one or more electrical (or optical) signals 406a, 406b, each representative of a different characteristic of the heart of the patient 402. For example, in some embodiments, the one or more sensors 404 comprise one or more electrical contacts, the signals 404a, 404b comprise electrical signals associated with the heart of the patient, the heart characteristic measurement system 406 is an electrocardiogram (EKG) system, and the one or more signals 406a, 406b comprise one or more types of electrocardiogram signals.

However in some other embodiments, the one or more sensors 404 can be comprised of a plurality of different types of sensors, for example, one or more of: electrical contacts, a blood oxygen sensor (e.g., an optical sensor), a blood pressure sensor, or a respiration sensor.

Accordingly, in some embodiments the heart characteristic measurement system 406 comprises one or more different types of measurement systems, for example, one or more of: an electrocardiogram (EKG), a blood oxygen measurement system, a blood pressure measurement system, or a respiration measurement system, and the one or more signals 406a, 406b comprise different types of signals, for example, one or more of: an EKG signal a blood oxygen level signal, a blood pressure signal, or a respiration signal.

The one or more signals 406a, 406b are received by a physiological abnormality processor 401.

As described above in conjunction with FIGS. 2 and 3, the processor 401 can operate to generate two different sequences of values, or one sequence of values. Options for couplings described below will be understood from the discussion above in conjunction with FIGS. 2 and 3.

The processor can use the same types of values to generate the two different sequences of values, or the processor 401 can use different types of values to generate the two different sequences of values. To these ends, in some embodiments, the processor 401 can include first and second different sequence generators 408, 418, configured to generate first and second sequences of values 408a, 418a, respectively. However, in some embodiments, the first and second sequence generators can be the same, in which case, the second sequence generator 418 need not be used.

The processor 401 can include first and second time window selectors 410, 420a, respectively, configured to receive the first and second sequences of values 406a, 416a and to generate first and second sets of values 410a, 420a, respectively. However, in some embodiments, the second time window selector 420 is coupled to receive the first sequence of values 408a. In some embodiments, the second time window selector 418 is not used and all processing takes place upon the first set of values 410a.

The processor 401 can include first and second time window sliders 412, 422 coupled to receive the first and second sets of values 412a, 422a, respectively, and configured to generate first and second pluralities of sets of values in accordance with the description above in conjunction with FIG. 3. However, in some embodiments, the second time window slider 422 is not used and only the first plurality of sets of values 412a is generated.

The processor 401 can also include a chaos detector coupled to receive the first plurality of sets of values 412a, or alternatively, coupled to receive the first set of values 410a. The chaos detector 414 is configured to generate a chaos signal 414a representative of a relative magnitude of chaos in the signal 406a. In some embodiments, the chaos detector 414 uses the above-described noise titration technique (further described below in conjunction with FIGS. 6 and 6A).

The processor 401 can also include a power spectrum analyzer 424 coupled to receive the second plurality of sets of values 422a, and/or optionally, the second set of values 420a, the first set of values 410a, or the first plurality of sets of values 412a.

The power spectrum analyzer 424 is configured to generate a power spectrum from the received values, to select a portion of the power spectrum and to generate a signal 424a representative of a magnitude (or power) of the selected portion of the power spectrum. In some embodiments, the selected portion can be the above-described HF portion. In other embodiments, the selected portion can be the above-described LF portion. In other embodiments, the selected portion can be the entire power spectrum.

The processor 401 can include a physiological abnormality categorizer 416 coupled to receive the signals 414a and 424a and configured to generate a signal 416a indicative of a detected physiological abnormality. The variety of ways that the physiological abnormality categorizer 416 can detect a physiological abnormality should be apparent from the discussion above in conjunction with FIGS. 2 and 3.

A display 426 can be coupled to receive the signal 426a and configured to generate a graphical display that can provide information about the detected physiological abnormality.

An alarm 428, e.g., and audible or visual alarm, can be coupled to receive the signal 426a and configured to generate an alarm that can alert a user to the physiological abnormality.

A memory 430 can be coupled to the processor 401. The memory 430 can include a program memory configured to store program instructions and to provide the program instructions to the processor 401. The memory 430 can also include a random access memory configured to store and provide data to the processor 401.

In some embodiments, the physiological abnormality is sleep apnea. In other embodiments, the physiological abnormality is chronic or acute heart failure). However, other physiological abnormalities may be detected with the methods described herein.

Figure 5:
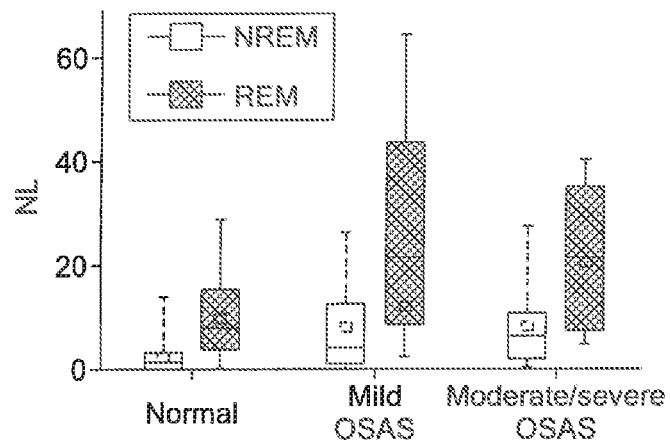
FIG. 5 is a graph showing processed data pertaining to heart interbeat interval chaos of normal patients who have no obstructive sleep apnea syndrome (OSAS), who have mild OSAS, and who have moderate or severe OSAS during rapid eye movement (REM) sleep and during non-REM sleep.
Figure 5A:
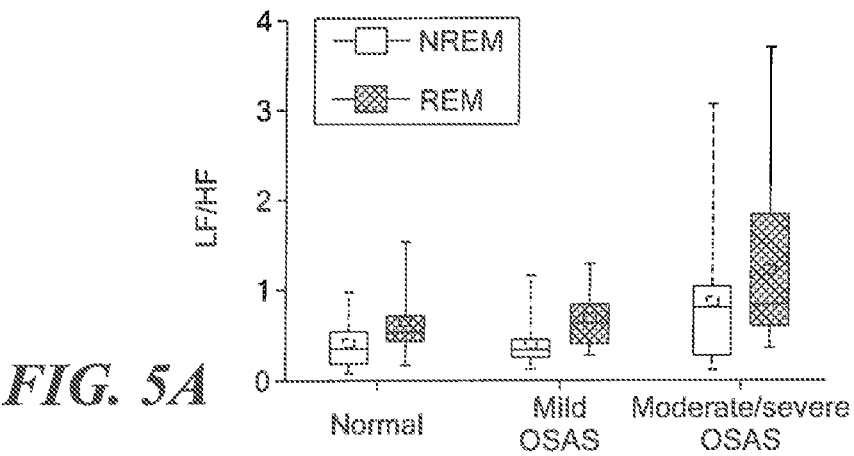
FIG. 5A is a graph showing processed data pertaining to high frequency power spectrum of heart interbeat intervals of normal patients who have no obstructive sleep apnea syndrome (OSAS), who have mild OSAS, and who have moderate or severe OSAS during rapid eye movement (REM) sleep and during non-REM sleep.
Figure 5B:
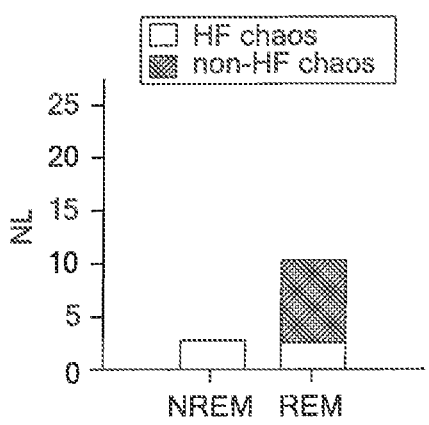
FIG. 5B is a graph showing processed data pertaining to combinations of heart interbeat interval chaos with high frequency power spectrum of heart interbeat intervals of normal patients who have no obstructive sleep apnea syndrome (OSAS), both for REM and non-REM sleep.
Figure 5C:
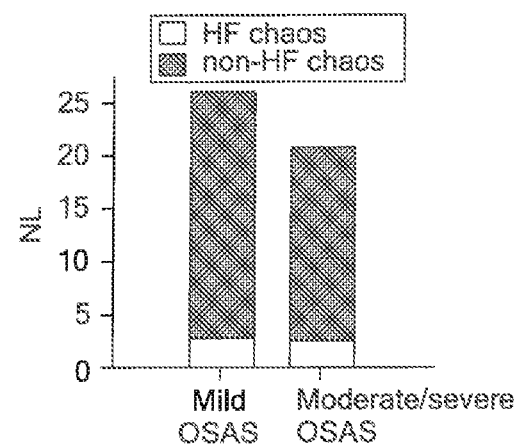
FIG. 5C is a graph showing processed data pertaining to combinations of heart interbeat interval chaos with high frequency power spectrum of heart interbeat intervals of patients who have mild and moderate/severe obstructive sleep apnea syndrome (OSAS), for REM sleep.

Referring now to FIGS. 5-5C, various test study results using real patients are shown.

Test subjects enrolled in the study underwent a comprehensive overnight polysomnogram evaluation of obstructive apnea.

The phrase "obstructive apnea" as used herein is defined as cessation of oronasal airflow in the presence of respiratory efforts for at least two respiratory cycle times. The phrase "obstructive hypopnea" as used herein is defined as a reduction in amplitude of oronasal airflow of greater than or equal to fifty percent, accompanied by at least a four percent oxygen desaturation and/or arousal. Obstructive sleep apnea syndrome (OSAS) as used herein includes both obstructive apnea and obstructive hypopnea.

As used herein, the phrase "apnea-hypopnea index (AHI)" is defined as the number of obstructive apnea and hypopnea events per hour of sleep. Obstructive sleep apnea syndrome (OSAS) was classified into two severity levels: mild (AHI=one to five per hour) and moderate/severe (AHI>five per hour).

The study population comprised fifty-two subjects with ages from one to sixteen years. Sixteen subjects were classified as having moderate/severe OSAS, eighteen subjects were classified as having mild/borderline OSAS, and eighteen subjects were classified as being normal with no OSAS. The normal group included ten children who had no history of sleep disorders and eight others who presented to the clinic with symptoms sufficient to warrant a sleep study, which subsequently showed that they neither snored, nor had apnea. All subjects were free of lung or neuromuscular disease, cardiac pathology or arrhythmia.

Sleep stages were scored using thirty second epochs (i.e., the above-described time windows). For each subject, continuous three-hour ECG recordings were collected in the middle of the night that demonstrated minimal missing data and movement artifacts. In preliminary analyses it was found that there were no significant differences between NL values (i.e., chaos) in stage two and in slow-wave sleep. Accordingly, all data in these sleep stages were combined as non-rapid eye movement (NREM) sleep. The three hour recording included at least one continuous ten minute segment of each of REM and NREM sleep. To minimize sampling bias, the three-hour recordings were carefully selected to capture apnea/hypopnea events consistent with the all-night AHI of the OSAS patients.

An ECG output signal was digitized at a sampling rate of 100 Hz. The fiducial points (i.e., peaks) of the R-waves were detected using a Hilbert transform-based peak extraction algorithm. The R-wave to R-wave interval (RRI) sequence of values was derived by calculating the sequential intervals between consecutive QRS peaks. The RRI was visually inspected for artifacts, and ECG segments that were clearly non-physiological were removed. No attempt was made to distinguish normal sinus beats from ectopic beats. The RRI time series was converted into equally-spaced samples in time by cubic-spline interpolation with a sampling rate of 4 Hz. All data manipulation and analysis algorithms were implemented in MATLAB® (The MathWorks®, Inc., Natick, Mass.).

Power spectrum of heart rate variability (HRV) was estimated by using the discrete Wigner-Ville transform, which allows continuous tracking of the changes in frequency and amplitude of each spectral component. The Wigner-Ville transform was applied to the RRI sequence of values with a five minute time window that was slid at thirty second intervals. From each spectrum, the power was calculated in two frequency bands: low frequency (LF), from 0.04 Hz to 0.15 Hz; and high frequency (HF), from 0.15 Hz to 0.4 Hz. Because normalized LF and HF indices are mathematically redundant, only the absolute powers and the low-to high-frequency power ratio (LF/HF) were used. It was found that the LF and HF powers demonstrated log-normal distributions; hence the log transformed values [ln (LF) and ln(HF)] were analyzed instead.

The above-described noise titration technique was used to assess changes in chaotic dynamics in the noise-contaminated heart beat interval sequence of values. Noise titration was applied on the RRI sequence of values with a five minute time window that was slid at thirty second intervals. The resulting titration index, i.e., the noise limit (NL), provides a measure of the relative level of chaos in HRV within each time window.

The apnea-hypopnea index (AHI) for the three subject groups were: moderate/severe OSAS, 21.6±20.5 events per hour (mean±SD); mild OSAS, 2.1±1.3 events per hour, and normal subjects, 0.2±0.3 events per hour.

Referring now to FIG. 5, a graph has a vertical axis with a scale in units of NL (i.e., relative chaos) in arbitrary units. The graph has a horizontal axis that identifies normal subjects, mild OSAS subjects, and moderate/severe OSAS subjects. For each type of subject, NL (i.e., chaos) at both REM sleep and NREM sleep is shown. Vertical bars are indicative of a range of NL for the various subjects in each subject type category. A horizontal division within each vertical bar is indicative of a median NL.

It can be seen that chaos, i.e., a quantified by mean NL, was significantly increased during REM sleep compared to NREM sleep in approximately eighty-eight percent of children studied regardless of OSAS severity. Importantly, not only did all subject groups show increases in mean NL from NREM to REM sleep (p<0.001), but the increases were significantly larger in OSAS compared to the normal group. (p=p-value for hypothesis testing, where a p-value less than 0.05 indicates a statistically significant result) Although the changes in mean NL with OSAS levels were quite variable among subjects, NL was a significant predictor for OSAS when interaction with sleep state was taken into account.

Referring now to FIG. 5A, a graph has a vertical axis with a scale in units of power ration, namely low frequency to high frequency power ratio, LF/HF, in arbitrary units. Thus, a higher number on the vertical axis represents a lower HF power (or a higher LF power, which was found not to be the case). The graph has a horizontal axis that identifies normal subjects, mild OSAS subjects, and moderate/severe OSAS subjects. For each type of subject, LF/HF at both REM sleep and NREM sleep is shown. Vertical bars are indicative of a range of LF/HF ratios for the various subjects in each subject type category. A horizontal division within each vertical bar is indicative of a median LF/HF ratio.

Adjusting for OSAS severity, mean LF/HF ratio was significantly increased in REM sleep compared with NREM sleep (p=0.001). The increase in mean LF/HF reflects primarily a decrease in ln(HF) (p<0.001) indicating parasympathetic withdrawal, with no change in ln(LF). The LF/HF ratio was also affected by OSAS although corresponding effects on ln(HF) and ln(LF) were not discernible. Thus LF/HF is a more sensitive indicator of cardiac-autonomic irregularity than the HF or LF component alone. Adjusting for sleep states, mean LF/HF was significantly higher in moderate/severe OSAS patients compared with normal subjects (p<0.001), but not in mild OSAS patients compared with normal subjects.

The concomitant increases in NL and in the LF/HF ratio during REM sleep and with OSAS with corresponding decreases or no change in ln(HF) suggest that the increases in NL in these conditions were not correlated to the parasympathetic-mediated HF component (HF chaos).

As used herein and as used in FIGS. 5B and 5C below, the term "non-HF chaos" refers to an increase in NL, i.e., chaos, at the same time as a decrease (or no change) in HF power level, either as reflected directly in an HF power measurement or as reflected in an LF/HF power ratio. Conversely, as used herein and as used in FIGS. 5B and 5C, the term "HF chaos" refers to an increase in NL, i.e., chaos, at the same time as an increase in HF power level, either as reflected directly in an HF power measurement or as reflected in an LF/HF power ratio.

Referring now to FIG. 5B, a graph has a vertical axes with scales in units of NL (i.e., relative chaos) in arbitrary units. The graph in FIG. 5B also has a horizontal axis with scale indicative of non-REM (NREM) and REM sleep. Vertical bars are indicative of a range of NL, i.e., chaos, for the all of the subjects during NREM and REM sleep. A horizontal division within each vertical bar is indicative of a partition between calculated non-HF chaos and HF chaos.

Referring now to FIG. 5C, a graph also has a vertical axes with scales in units of NL (i.e., relative chaos) in arbitrary units. However, the graph in FIG. 5C has a horizontal axis with scale indicative of categories of subjects, in particular those with mild OSAS and those with moderate/severe OSAS. Vertical bars are indicative of a range of NL, i.e., chaos, for the two categories of subjects, mild and moderate/severe. A horizontal division within each vertical bar is indicative of a partition between calculated non-HF chaos and HF chaos.

The indicated non-HF chaos reveals changing cardiac sympathetic-parasympathetic activities that are not discernible by conventional HRV analyses.

To determine whether such non-HF chaos may detect OSAS independent of polysomnogram data, various heart rate variability (HRV) metrics, including some conventional HRV metrics, for all subjects were evaluated over the full 3-hour segments without separating into different sleep stages. Only NL (i.e. chaos) and the LF/HF ratio showed significant differences between the moderate/severe OSAS group and the control group. NL is the only metric that achieved statistical significance (p<0.05) between the mild OSAS group and the control group.

FIGS. 5-5C provide evidence that non-HF chaos may reveal changes in cardiac sympathetic-parasympathetic activities that are not discernible by conventional HRV metrics alone. Specifically, the increases in NL with concomitant decreases (or no change) in HF power and/or increases in LF/HF suggest that such non-HF chaos is not correlated with the HF component or respiratory sinus arrhythmia. Furthermore, although NL and LF/HF were both significantly elevated over mixed sleep stages in children with moderate/severe OSAS (AHI>five per hour), only NL was able to differentiate between mild OSAS (one<AHI<five per hour) and normal controls (AHI<one per hour) with demonstrable sensitivity, specificity, positive predictivity, and negative predictivity).

The ability of the non-HF heart rate chaos technique described herein to identify children with even mild OSAS provides a method and apparatus screening and intervention of the condition. Such early noninvasive detection of OSAS-dependent cardiac-autonomic abnormalities represents significant advancements in electrocardiology and pediatric sleep medicine insofar as even mild OSAS may be associated with considerable neurocognitive morbidity in children despite the subtlety of daytime symptoms.

Past studies in adult subjects have shown that normal heart rate chaos (with NL>zero) during nighttime may be attributed in large part to HF chaos. Nocturnal increases in HF power and decreases in LF/HF have been reported in pediatric subjects mainly during NREM sleep, particularly slow-wave sleep. Therefore, in past studies, the heart rate chaos found in children during NREM sleep most likely reflects parasympathetic-mediated HF chaos (see, e.g., FIG. 5C), in agreement with the past studies for adults.[2]

In contrast, the present data represented in FIGS. 5-5C shows that NL (i.e., chaos) was even higher during REM than NREM sleep. This was despite a corresponding decrease in HF power and increase in LF/HF. Thus, it may be reasonably concluded that such non-HF chaos during REM sleep had a predominantly sympathetic instead of parasympathetic mediation. In support of this conclusion, REM sleep in adults is known to be associated with intermittent, strong and variable sympathetic bursts causing marked cardiorespiratory disturbances. The latter may contribute to the non-HF chaos in children during REM sleep.

Likewise, the present data represented in FIGS. 5-5C shows that NL (i.e., chaos) was significantly increased (particularly during REM sleep) while HF power was virtually unchanged (or even decreased) in children with OSAS, a pathological condition that is known to provoke persistent elevation of sympathetic activity in adults. The interaction effects between OSAS and REM sleep for NL is consistent with the preponderance of apnea episodes during REM sleep in children with OSAS. Again, such OSAS-dependent increase in non-HF chaos (FIG. 5C) is consistent with a predominantly sympathetic instead of parasympathetic mediation. Adding to this notion, a similar trend of paradoxical intermittent increases in NL in combination with decreased HF power and increased LF/HF can be found in patients with congestive heart failure, another pathological condition that is characterized by sympathoexcitation and parasympathetic impairment. The strikingly consistent pattern of increases in NL concomitant with attenuated or unchanged HF power and increased LF/HF in REM sleep, OSAS and congestive heart failure, when taken together, strongly suggest that non-HF chaos is a selective marker of sympathoexcitation in these conditions.

By contrast, the results show that such REM sleep- and OSAS-dependent increase in non-HF chaos was accompanied by little or no change in ln(LF) in children, consistent with the fact that LF power is generally a poor marker of sympathetic activity.

The LF/HF ratio is generally a more sensitive indicator of cardiac-autonomic irregularity than LF or HF power alone, it is again nonspecific to sympathetic activity and insensitive to mild OSAS. No conventional time-domain, frequency-domain, or geometric HRV metrics is sensitive or specific to the REM sleep- and OSAS-dependent sympathoexcitation or demonstrated interaction effects of OSAS and REM sleep, and none of them is able to detect mild OSAS in children.

In conclusion, non-HF chaos is a selective noninvasive marker of the sympathoexcitation associated with REM sleep, OSAS, and other conditions. The presently demonstrated sensitivity and specificity of non-HF chaos in tracking REM sleep- and OSAS-dependent autonomic abnormalities open the possibility of a home screening test of sympathetic-parasympathetic imbalance for early diagnosis of pediatric and adult OSAS and a wide range of cardiovascular diseases.

While use of HF chaos to detect sleep apnea is described in data above, it is possible to detect other physiological abnormalities by combining detected elevated chaos with other quantifiable characteristics described in conjunction with FIGS. 2 and 3.

Returning now to the subject of detection and characterization of chaos, as described above, in some embodiments, chaos can be identified in a sequence of values using the above-described "noise titration" technique.

Typically, an autonomous (i.e., non-driven and time-invariant), dynamical system can be described as a black box having an input sequence $X_n$ and an output sequence $y_n$ at time n=1, ..., N in multiples of the sampling time T. The noise-titration algorithm can use a closed-loop version of the Volterra series in which the output $y_n$ loops back as a delayed input (i.e., $X_n=y_{n-1}$) may be used to represent the dynamical system including those dynamical systems provided as strictly autonomous dynamical systems or dynamical systems which have been reformulated as such. Within this framework, a univariate time series may be analyzed by using a discrete Volterra-Wiener-Korenberg series of degree d and memory k as a model to calculate a predicted time series $y_n^{calc}$ as shown in Equation (1) below:

$$y_n^{calc} = a_o + a_1 y_{n-1} + a_2 y_{n-2} + \ldots a_k + a_1 y_{n-k} + a_{k+1} y_{n-1}^2 + \quad \text{(Equation 1)}$$
$$a_{k-2} y_{n-1} y_{n-2} + \ldots a_{M-1} y_{n-k}^d$$
$$= \sum_{m=0}^{M-1} a_m z_m(n)$$

in which:
$a_n$=coefficients of the polynomial for n=0 to N;
k=an embedding dimension;

d=the degree of the polynomial function (i.e. the degree of nonlinearity of the model);
M=a total dimension of the equation and may be computed as:

$$M=(k+d)!/(d!k!).$$

It should be noted that other forms of functional expansions are also possible. For example block-structured models may also be used. As can be seen from Equation (1) the set $\{z_m(n)\}$ represents a functional basis composed of all the distinct combinations of the embedding space coordinates $(v_{n-1}, t_{n-2}, \ldots, y_{n-k})$ up to degree d, having a total dimension M. Thus, each model is parameterized by the embedding dimension k and the degree of the nonlinearity of the model d.

A recursive procedure is preferably used to estimate the values of the coefficients $a_m$. In a preferred embodiment, a Gram-Schmidt procedure from linear and nonlinear autocorrelations of the original data series itself may be used to compute values for the coefficients $a_m$. Those of ordinary skill in the art will recognize of course that other recursive and nonrecursive techniques may also be used to compute values of the coefficient $a_m$. Such computations may be performed, for example, on a workstation.

Next, a performance measure is computed for each of the models. For example, a short-term prediction power of a model may be measured by computing a one-step-ahead prediction error in accordance with Equation (2):

$$\epsilon(k, d)^2 = \frac{\sum_{n-1}^{N} (y_2^{calc}(k, d) - y_n)^2}{\sum_{n-1}^{N} (y_n - \bar{y})^2} \quad \text{Equation (2)}$$

in which:
$\epsilon(k, d)^2$ is a value which corresponds to a normalized variance of the error residuals; and
y may be computed as:

$$\bar{y} = \frac{1}{N} \sum_{n-1}^{N} y_n \quad \text{Equation (3)}$$

Once all of the models are computed or as the models are being computed, a search is performed to identify an optimum model $\{k_{opt}, d_{opt}\}$. The optimum model may be defined, for example, as the model which minimizes the following information criterion in accordance with the parsimony principle:

$$C(r)=\log\ e(r)+r/N \quad \text{Equation (4)}$$

where:
r∈[1, M] is the number of polynomial terms of the truncated Volterra expansions from a certain pair of embedding dimension values and degree of nonlinearity of the model (k,d).

Those of ordinary skill in the art will appreciate of course that other information criteria may also be used. The numerical procedure using the above information criteria is as follows: For each data series, identify the best linear model by searching for the linear model having an embedding dimension value in which minimizes the performance measure C(r). It should be noted that the linear models are those models in which the degree of the polynomial function is 1 (i.e. d=1).

Similarly, the nonlinear model having an embedding dimension value k.sup.nl which minimizes the performance measure C(r) is identified. It should be noted that the nonlinear models are those models in which the degree of the polynomial function is greater than 1 (i.e. d>1).

Next surrogate randomized data sets with the same autocorrelation (and power spectrum) as the original series are generated and optimum linear and nonlinear models are identified for the surrogate data sets. This results in four competing models having the following error standard deviations the surrogate data sets. This results in four competing models having the following error standard deviations $$\epsilon_{orig}^{lin}, \epsilon_{orig}^{nl}, \epsilon_{surr}^{lin}, \epsilon_{surr}^{nl}$$

in which
- $\epsilon$ corresponds to the standard deviation;
- the superscript lin denotes a linear model;
- the superscript nl denotes a nonlinear model;
- the subscript orig denotes an original data sequence; and
- the subscript surr denotes a surrogate data sequence.

From above, the presence of nonlinear determinism is indicated if the optimum model (i.e. the model which minimizes the information criterion given above) has a polynomial of degree greater than 1 (i.e., $d_{opt}>1$). Further corroboration may be obtained with the following objective statistical criteria: For models having Gaussian residuals, a standard F-test will serve to reject, with a certain level of confidence, the hypothesis that nonlinear models are not better than linear models as one-step-ahead predictors. This Gaussian assumption may be tested by using an $x^2$-test with a 99% cutoff.

Alternatively, the results may be confirmed using a non-parametric Mann-Whitney rank-sum statistic, which does not depend on a Gaussian assumption. Under this scheme, the relevance of nonlinear predictors is established when the best nonlinear model from the original data is significantly more predictive than both (a) the best linear model from the data series, and (b) the best linear and nonlinear models obtained from the surrogate series. This may be expressed as:

$$\epsilon_{orig}^{lin}, \epsilon_{surr}^{nl}, \epsilon_{surr}^{lin} > \epsilon_{orig}^{nl}$$

where the comparisons are made in the statistical sense.

It should, however, be noted that since surrogate data are generated by preserving only the linear autocorrelation function of the data series (nonlinear autocorrelations are randomized), the addition of nonlinear terms does not increase the prediction power and the one step ahead prediction error for the nonlinear model using the surrogate data set is approximately equal to the one step ahead prediction error for the linear model using the surrogate data set. This may be expressed as:

$$\epsilon_{surr}^{lin} \approx \epsilon_{surr}^{lin}$$

Furthermore, surrogate data are always best approximated by a linear model.

Figure 6:
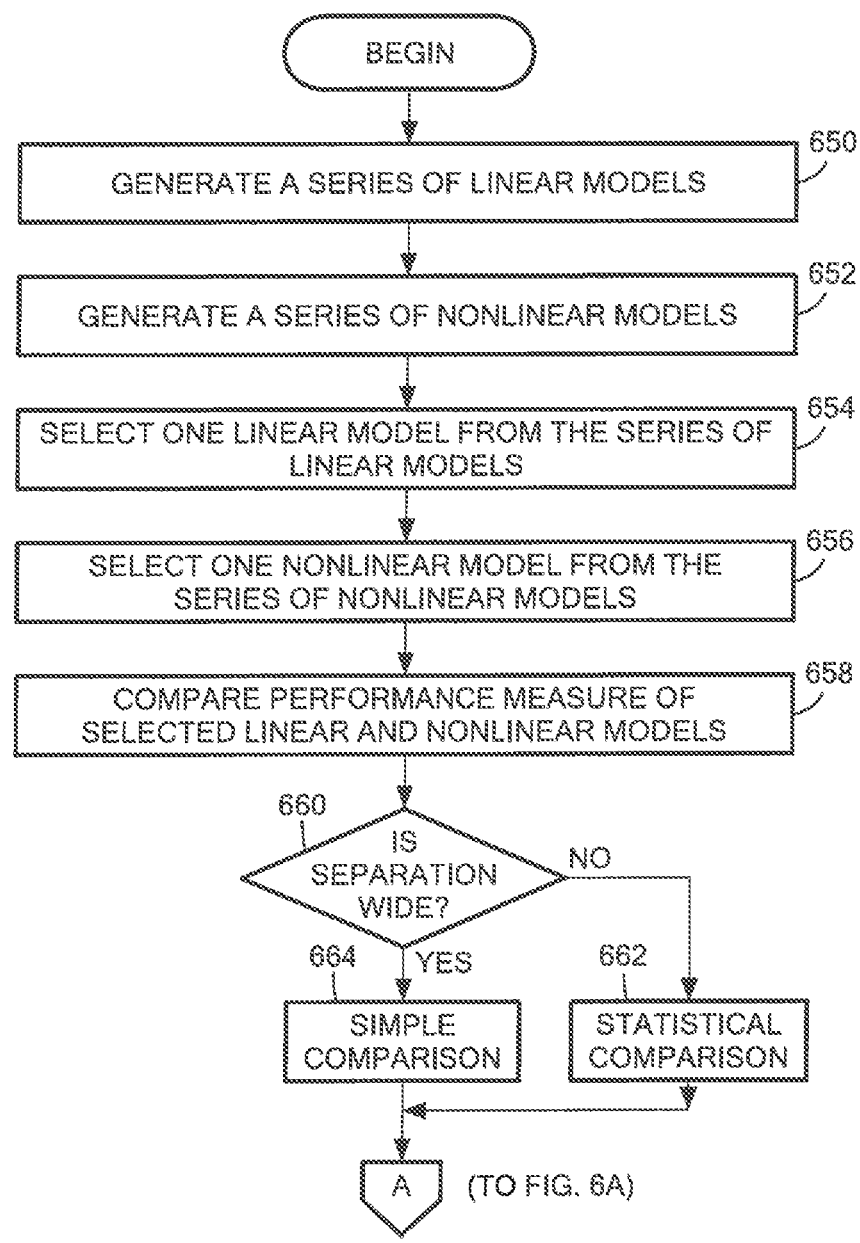
FIGS. 6 and 6A taken together show a summary of a noise titration technique used to identify a relative magnitude of heart interbeat interval chaos.
Figure 6A:
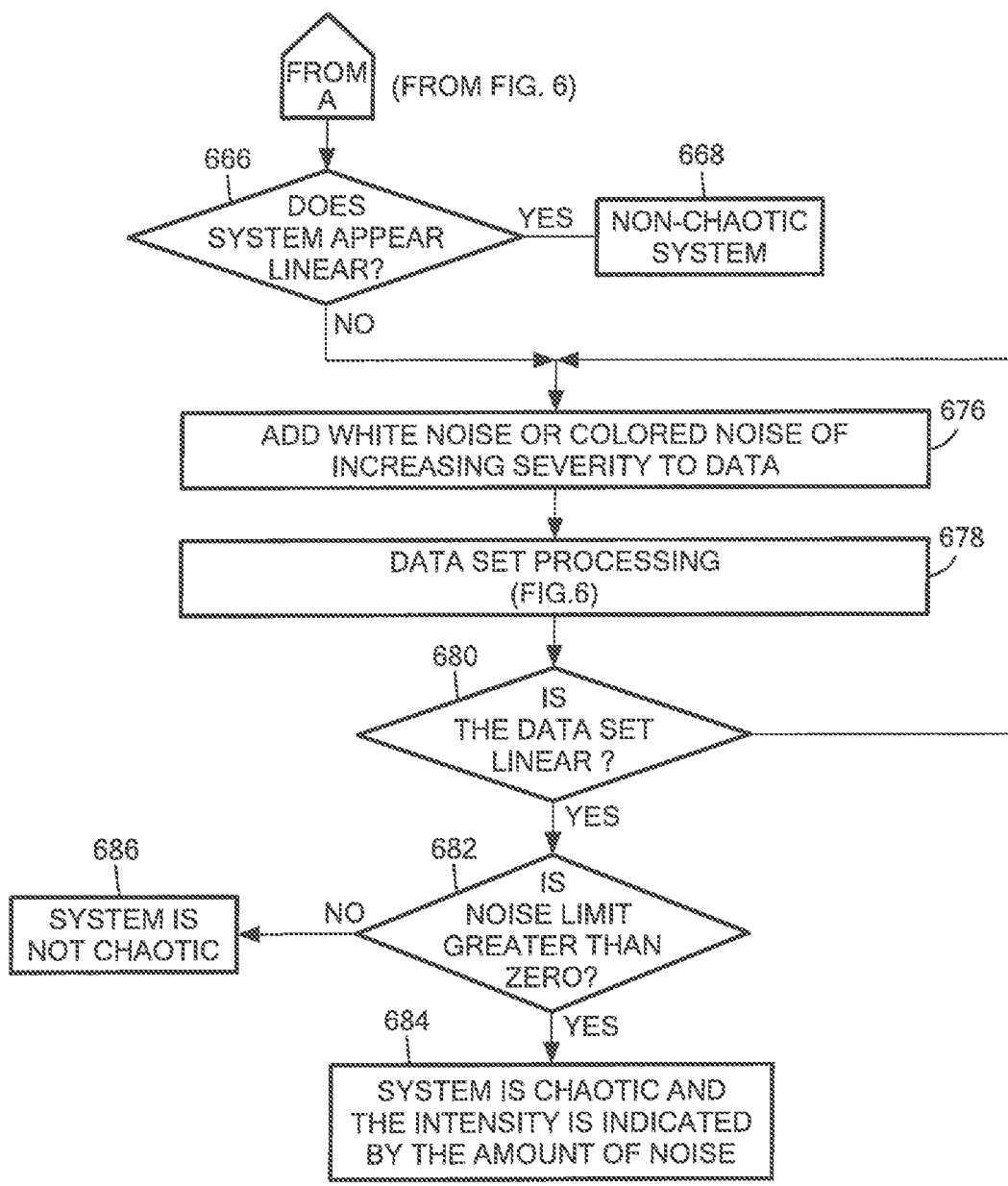

Referring now to FIGS. 6 and 6A, a method is illustrated for determining whether a signal generated by an autonomous (i.e., non-driven and time-invariant), dynamical system includes nonlinear components and further for determining whether the nonlinear dynamical system is chaotic and to what extent.

As shown in blocks 650 and 652, a series of linear models and nonlinear models are obtained for a data sequence. The data sequence may be collected and stored in a storage device or alternatively the data sequence may be collected and the linear and nonlinear models may be generated in real time in ways described above. In one embodiment, the linear and nonlinear models may be provided as a closed-looped version of the Volterra-Wiener-Korenberg series discussed above, for which an output value $y_n$ loops back as a delayed input (i.e., $x_n=y_{n-1}$). Those of ordinary skill in the art will recognize of course that any technique may be used to provide the models. For example, the models may be provided using a so-called block-structured procedure, a Lee-Schetzen procedure, a least squares procedure or any other recursive procedure well known to those of ordinary skill in the art. Other possible alternatives to the Volterra-Wiener-Korenberg series include neural nets, radial basis function networks, and local embedding maps. The Volterra-Wiener-Korenberg series discussed above, however, provides a computationally efficient and statistically stable technique for modeling the data. Such a computationally efficient and statistically stable technique is desirable to use in systems in which it is desirable to process noise corrupted data in real time.

Next, as shown in block 654, a particular linear model is selected from the series of linear models generated in block 650. To select the linear model, a performance measure of each of the linear models is selected and computed. The performance measure of each of the linear models are compared to each other. The particular linear model which is selected is the linear model having a preferred performance measure. It should be noted that in some applications the preferred performance measure may be specifically selected by a user of the system and may not necessarily correspond to an optimum or best performance measure. The selected linear model has a preferred performance measure.

Similarly, as shown in block 656, a particular one of the nonlinear models is selected from the series of nonlinear models generated in block 652. To select the particular nonlinear model, a performance measure of the model is identified and this performance measure is computed for each of the nonlinear models in the series of nonlinear models. The computed performance measures are compared and the nonlinear model having a preferred performance measure is selected. It should be noted that in some applications, the preferred performance measure may not correspond to an optimum or best performance measure.

It should be noted that any one of a plurality of performance measures including but not limited to the Akaike Information Criteria (AIC), a minimum description length measure, a log livelihood measure and a residual sum of square errors may also be used. The selection of a particular performance measure depends upon a variety of factors including but not limited to the particular type of system being analyzed (e.g. biological system, economic system, social system, etc.), the particular type of signal being analyzed and the type of noise present noted that in some applications it may be desirable to use more than one performance measure. For example multiple performance measures may be used to aid in the determination of whether a system is linear or nonlinear. In this case a plurality of different criteria (e.g. three criteria) may be monitored and if a majority of the plurality of the criteria (e.g. two out of the three criteria) indicate that the data is nonlinear then the decision is made that the data is nonlinear.

The performance measures of the selected linear and nonlinear models having the preferred performance measures are then compared as shown in block 658. Next, as shown in decision block 660, a decision is made as to whether the separation between the performance measures of the selected linear and nonlinear models is relatively wide.

In the event that the performance measures are separated by a relatively wide distance, then a relatively simple comparison technique can be used to compare the two values in block 664. Alternatively however, if the performance measures are not separated by a relatively wide distance, then it may be desirable to use a statistical approach to compare the two performance measures as shown in block 662.

In block 666 (FIG. 6A), it is determined whether the system appears linear based on the comparison of the performance measures of the selected linear and nonlinear models. That is, if the selected linear model represents the system from which the data set is taken better than the selected nonlinear model, then the system is determined to be linear; whereas, if the nonlinear model represents the system better than the linear model, then the system is determined to be nonlinear. As one example, in applications in which the performance measure used is the AIC value, then a lower AIC value indicates a better representation of the system than a higher AIC value, as described above in conjunction with FIG. 2.

If, based on the comparison of performance measures in block 666, the system is determined to be linear, then the system can be characterized as non-chaotic as shown in block 668. Alternatively, if the system does not appear to be linear, then processing continues in order to determine whether the nonlinear system is chaotic or has periodic or quasi-periodic limit cycles.

More particularly, there are four possible states of an autonomous (non-driven and time-invariant) nonlinear system: (1) chaotic; (2) periodic; (3) quasi-periodic; and (4) equilibrium. If in block 666, a decision is made that the system is nonlinear, it is desirable to further process the data to determine whether the nonlinear system is chaotic and, if so, to what extent. This is because the strength of chaos detected in certain biological systems, such as systems represented by an electrocardiograph signal, has a high correlation to cardiac health. In particular, it has been recognized that the electrocardiograph signals of healthy cardiac patients exhibit a high degree of chaos, whereas patients with compromised cardiac health, such as those with congestive heart failure (CHF), generally have electrocardiograph signals exhibiting significantly less chaos. To this end, blocks 676-684 illustrate a preferred way of determining whether the nonlinear system is chaotic and, further, for providing an indication of the relative strength of detected chaos. Blocks 670-674 illustrate an optional, additional way of determining whether the nonlinear system is chaotic or has periodic or quasi-periodic limit cycles. That is, blocks 670-674 illustrate a processing technique for detecting strange non-chaotic attractors and quasi-periodic systems. In applications in which it desirable to perform blocks 670-674 in addition to blocks 676-684, the two sets of blocks may be performed simultaneously or sequentially.

Considering first the method of blocks 676-684, a noise signal is added to the data set generated from a signal of the analyzed system in block 676. Various types of noise signals are suitable, including white noise or colored noise. The noise signal is selected to have a predetermined standard deviation (.sigma.). It will be appreciated by those of ordinary skill in the art that the standard deviation of the noise signal is selected based on a variety of factors including permissible computation time (i.e., since the smaller the standard deviation, the more noise increments that have to be added and thus, the longer the computation time) and the separation between the linear model and nonlinear model curves. That is, if a relatively large separation exists between the curves, then a noise signal having a relatively large standard deviation may be used. The result of block 676 is a test signal which differs from the data set representing the analyzed system by the addition of the noise signal.

In block 678, the test signal is processed in the manner described in conjunction with FIGS. 2 and 6. That is, series of linear and nonlinear models are generated from the test signal, one of the linear models and one of the nonlinear models is selected based on a preferred performance measure and the performance measures of the selected linear and nonlinear models are compared. Further, a determination is made as to whether the separation between the performance measures of the selected linear and nonlinear models is relatively wide and an appropriate comparison is made between such performance measures as a function of their separation, as described above.

In block 680, it is determined whether the test signal data set appears linear. This determination is based on whether the performance measure of the selected linear model better represents the system than the performance measure of the selected nonlinear model, as described above. If the test signal data set does not appear linear, then blocks 676-678 are repeated, as shown. That is, additional noise of increasing intensity is added to the test signal to generate a next test signal and the next test signal is processed in block 678 as described above.

Blocks 676-680 continue to be repeated until a determination is made in block 680 that the test signal data set appears linear. Thus, the processing loop of blocks 676-680 results in noise of increasing severity being added to the original data set representing the analyzed system until the resulting test signal data set is linear.

In decision block 682, it is determined whether the noise limit of the test signal data set is greater than zero. The noise limit is defined as the maximum standard deviation (a) at which nonlinearity in the signal is detected. If the test signal which is determined to represent a linear system in block 680 has a noise limit greater than zero, then the dynamical system is determined to be chaotic in block 684. Alternatively, if the noise limit of the test signal is approximately zero, then the system is determined to be nonlinear with periodic or quasi-periodic limit cycles in block 674.

Further, the relative strength of the chaos is indicated by the amount of noise added (i.e., the above describe noise limit, NL) to the data set in order to generate the linear test signal. In particular, the noise level is roughly proportional to the strength of the chaos, with the proportionality constant being a function of the system. The chaos strength thus provided can be used in further process blocks described above in conjunction with FIGS. 2 and 3 to diagnose certain physiological abnormalities.

If, at block 682, the calculated noise limit (NL) is not greater than zero, then the system is determined not to be chaotic at block 686.

As described above, the maximum noise added before nonlinearity goes undetected is referred to herein as the noise limit (NL). Under the noise titration scheme, a noise limit greater than zero represents the detection of chaotic dynamics. In addition, the noise limit mirrors the maximal Lyapunov exponent of the system dynamics.

Having described preferred embodiments of the invention it will now become apparent to those of ordinary skill in the art that other embodiments incorporating these concepts may be used. Accordingly, it is submitted that that the invention should not be limited to the described embodiments but rather should be limited only by the spirit and scope of the appended claims.

Additionally, the software included as part of the invention may be embodied in a computer program product that includes a computer-readable storage medium and also a computer-readable transmission medium. The term computer-readable storage medium as used here is used to describe a computer-readable memory device or structure, such as a hard drive device, a CD-ROM, a DVD-ROM, or a computer diskette, having computer-readable program code segments stored thereon. Thus, as used herein, the term computer-readable storage medium is used to describe a tangible device or structure on which such computer-readable program code segments are stored. The term "computer-readable transmission medium" is used herein to describe a communications link, either optical, wired, or wireless, having computer-readable information carried thereon as digital or analog signals. Thus, as used herein, the term computer-readable transmission medium is used to describe a tangible device or structure upon which or through which such computer-readable information is communicated. The terms computer-readable storage medium and computer-readable transmission medium do not describe transitory computer signals, which are otherwise referred to herein as computer-readable signals.

All publications and references cited herein are expressly incorporated herein by reference in their entirety.

What is claimed is:

1. A method of detecting increased sympathetic activity indicative of a physiological abnormality, comprising:
   measuring, from a patient sensor, a quantifiable characteristic of a patient;
   quantifying, with a processor, a chaos of the quantifiable characteristic, wherein the quantified chaos comprises at least one of a chaos-like behavior or a non-linear dynamics relationship of the quantifiable characteristic;
   identifying, with the processor, an increasing chaos in accordance with the quantified chaos;
   identifying, with the processor, a non-increasing parasympathetic activity in the patient;
   combining, with the processor, the identified increasing chaos and the identified non-increasing parasympathetic activity to determine that the identified increasing chaos is a result of the increased sympathetic activity in the patient, the combining resulting in a more accurate determination that the identified increasing chaos is a result of the increased sympathetic activity, more accurate than either the identified increasing chaos or the identified non-increasing parasympathetic activity alone;
   detecting, with the processor, the physiological abnormality, wherein the detected physiological abnormality is of a type detectable by the increased sympathetic activity in the patient; and
   generating, with the processor, a signal indicative of the detected physiological abnormality.

2. The method of claim 1, wherein the measuring comprises:
   measuring a quantifiable characteristic of a heart of a patient with a heart sensor, wherein the quantifying the chaos comprises:
   generating a sequence of values representative of the characteristic of the heart; and
   selecting, with the processor, a first measurement time window corresponding to a first selected set of values within the sequence of values, wherein the identifying the increasing chaos comprises:
   analyzing, with the processor, the first selected set of values to identify the increasing chaos, wherein the identifying the non-increasing parasympathetic behavior comprises:
   selecting, with the processor, a second measurement time window corresponding to a second selected set of values within the sequence of values;
   analyzing, with the processor, the second selected set of values to generate a power spectrum;
   selecting, with the processor, a portion of the power spectrum; and
   analyzing, with the processor, the selected portion of the power spectrum to identify the non-increasing parasympathetic activity.

3. The method of claim 2, wherein the analyzing the first selected set of values comprises:
   analyzing, with the processor, the first selected set of values using a noise titration technique, wherein the noise titration technique results in a maximum tolerated noise level or noise limit (NL) indicative of a magnitude of the chaos.

4. The method of claim 3, wherein the quantifiable characteristic of the heart comprises at least one of a heart interbeat interval or a heart rate and, and wherein the sequence of values comprises a time series of heart interbeat interval values or a series of heart rate values.

5. The method of claim 4, wherein the selected portion of the power spectrum comprises a high frequency portion of the power spectrum.

6. The method of claim 5, wherein the analyzing, with the processor, the selected portion of the power spectrum to detect the magnitude of the selected portion of the power spectrum comprises:
   detecting an increase in the magnitude of the high frequency portion of the power spectrum to identify the non-increasing parasympathetic activity.

7. The method of claim 5, wherein the analyzing, with the processor, the selected portion of the power spectrum to detect the magnitude of the selected portion of the power spectrum comprises:
   detecting a lack of change or a decrease of the magnitude of the high frequency portion of the power spectrum to identify the non-increasing parasympathetic activity.

8. The method of claim 5, wherein the physiological abnormality is sleep apnea.

9. The method of claim 3, wherein the second measurement time window is the same as the first measurement time window, and wherein the second selected set of the sequence of values is the same as the first selected set of the sequence of values.

10. The method of claim 3, where the first measurement time window has a duration less than about five minutes and the second measurement time window has a duration less than about five minutes.

11. The method of claim 3, wherein the first selected set of the sequence of values includes about twelve hundred values with a sampling rate of about four Hertz, and wherein the second selected set of the sequence of values includes about twelve hundred values with a sampling rate of about four Hertz.

12. The method of claim 1, wherein the quantifying the chaos further comprises:

sliding, with the processor, the first measurement time window in time to collect a first plurality of sets of the sequence of values, wherein the identifying the increasing chaos further comprises:

analyzing, with the processor, the first plurality of sets of the sequence of values to identify the increasing chaos, wherein the identifying the non-increasing parasympathetic behavior further comprises;

sliding, with the processor, the second measurement time window in time to collect a second plurality of sets of the sequence of values;

analyzing, with the processor, the second plurality of sets of sequence of values to generate a changing power spectrum;

selecting, with the processor, a portion of the changing power spectrum; and analyzing, with the processor, the selected portion of the changing power spectrum to identify the non-increasing parasympathetic activity.

13. The method of claim 12, wherein the selected portion of the power spectrum comprises a high frequency portion of the changing power spectrum.

14. The method of claim 13, wherein the analyzing, with the processor, the selected portion of the changing power spectrum to detect the magnitude of the selected portion of the changing power spectrum comprises:

detecting an increase in the magnitude of the high frequency portion of the changing power spectrum to identify the non-increasing parasympathetic activity.

15. The method of claim 13, wherein the analyzing, with the processor, the selected portion of the changing power spectrum to detect the magnitude of the selected portion of the changing power spectrum comprises:

detecting a lack of change or a decrease of the magnitude of the high frequency portion of the changing power spectrum to identify the non-increasing parasympathetic activity.

16. The method of claim 13, wherein the physiological abnormality is sleep apnea.

17. The method of claim 12, wherein the second measurement time window is the same as the first measurement time window, and wherein the selected second plurality of sets of the sequence of values are the same as the selected first plurality of sets of the sequence of values.

18. The method of claim 12, where the first measurement time window has a duration less than about five minutes and the second measurement time window has a duration less than about five minutes.

19. The method of claim 12, wherein the selected first plurality of sets of the sequence of values includes about twelve hundred values with a sampling rate of about four Hertz, and wherein the second plurality of sets of the sequence of values includes about twelve hundred values with a sampling rate of about four Hertz.

20. A system to detect increased sympathetic activity indicative of a physiological abnormality, comprising:

a patient sensor coupled to a patient and configured to measure a quantifiable characteristic of a patient; and a processor, configured to:

quantify a chaos of the quantifiable characteristic, wherein the quantified chaos comprises at least one of a chaos-like behavior or a non-linear dynamics relationship of the quantifiable characteristic;

identify an increasing chaos in accordance with the quantified chaos;

identify a non-increasing parasympathetic activity in the patient; and combine the identified increasing chaos and the identified non-increasing parasympathetic activity to determine that the identified increasing chaos is a result of the increased sympathetic activity in the patient, the combination resulting in a more accurate determination that the identified increasing chaos is a result of the increased sympathetic activity, more accurate than either the identified increasing chaos or the identified non-increasing parasympathetic activity alone;

detect the physiological abnormality, wherein the detected physiological abnormality is of a type detectable by the increased sympathetic activity in the patient; and generate a signal indicative of the detected physiological abnormality.

21. The system of claim 20, wherein the patient sensor comprises a heart sensor configured to measure a quantifiable characteristic of a heart of a patient, wherein the processor is further configured to:

generate a sequence of values representative of the characteristic of the heart;

select a first measurement time window corresponding to a first selected set of values within the sequence of values;

analyze the first selected set of values to identify the increasing chaos;

select a second measurement time window corresponding to a second selected set of values within the sequence of values;

analyze the second selected set of values to generate a power spectrum;

select a portion of the power spectrum; and analyze the selected portion of the power spectrum to identify the non-increasing parasympathetic activity.

22. The system of claim 21, wherein the processor is configured to analyze the first selected set of values using a noise titration technique, wherein the noise titration technique results in a maximum noise level (NL) indicative of a magnitude of the chaos.

23. The system of claim 22, wherein the quantifiable characteristic of the heart comprises at least one of a heart interbeat interval or a heart rate and, and wherein the sequence of values comprises a time series of interval values or a series of heart rate values.

24. The system of claim 23, wherein the selected portion of the power spectrum comprises a high frequency portion of the power spectrum.

25. The system of claim 24, wherein the processor is configured to detect an increase in the magnitude of the high frequency portion of the power spectrum to identify the non-increasing parasympathetic activity.

26. The system of claim 24, wherein the processor is configured to detect a lack of change or a decrease of the magnitude of the high frequency portion of the power spectrum to identify the non-increasing parasympathetic activity.

27. The system of claim 24, wherein the physiological abnormality is sleep apnea.

28. The system of claim 22, wherein the second measurement time window is the same as the first measurement time window, and wherein the second selected set of the sequence of values is the same as the first selected set of the sequence of values.

29. The system of claim 22, where the first measurement time window has a duration less than about five minutes and the second measurement time window has a duration less than about five minutes.

30. The system of claim 22, wherein the processor is further configured to:
slide the first measurement time window in time to collect a first plurality of sets of the sequence of values;
analyze the first plurality of sets of the sequence of values to identify the increasing chaos;
slide the second measurement time window in time to collect a second plurality of sets of the sequence of values;
analyze the second plurality of sets of sequence of values to generate a changing power spectrum;
select a portion of the changing power spectrum; and
analyze the selected portion of the changing power spectrum to identify the non-increasing parasympathetic activity.

31. The system of claim 30, wherein the selected portion of the power spectrum comprises a high frequency portion of the power spectrum.

32. The system of claim 31, wherein the processor is configured to detect an increase in the magnitude of the high frequency portion of the changing power spectrum to identify the non-increasing parasympathetic activity.

33. The system of claim 31, wherein the processor is configured to detect a lack of change or a decrease of the magnitude of the high frequency portion of the changing power spectrum to identify the non-increasing parasympathetic activity.

34. The system of claim 31, wherein the physiological abnormality is sleep apnea.

35. The system of claim 30, wherein the second measurement time window is the same as the first measurement time window, and wherein the selected second plurality of sets of the sequence of values are the same as the selected first plurality of sets of the sequence of values.

36. The system of claim 30, where the first measurement time window has a duration less than about five minutes and the second measurement time window has a duration less than about five minutes.

37. The system of claim 30, wherein the selected first plurality of sets of the sequence of values includes about twelve hundred values with a sampling rate of about four Hertz, and wherein the second plurality of sets of the sequence of values includes about twelve hundred values with a sampling rate of about four Hertz.

38. The system of claim 20, wherein the processor is configured to identify the identified non-increasing parasympathetic activity in accordance with at least one of blood oxygenation values, blood pressure values, and/or respiration rate (or interval) values.

39. The system of claim 20, wherein the processor is configured to identify the identified non-increasing parasympathetic activity in accordance with a ratio of a low frequency (LF) power spectrum and a high frequency (HF) a power spectrum of the quantifiable characteristic.

40. A non-transitory computer readable storage medium comprising instructions for detecting increased sympathetic activity indicative of a physiological abnormality, the instructions comprising instructions for:
measuring, from a patient sensor, a quantifiable characteristic of a patient;
quantifying a chaos of the quantifiable characteristic, wherein the quantified chaos comprises at least one of a chaos-like behavior or a non-linear dynamics relationship of the quantifiable characteristic;
identifying an increasing chaos in accordance with the quantified chaos;
identifying a non-increasing parasympathetic activity in the patient; and
combining the identified increasing chaos and the identified non-increasing parasympathetic activity to determine that the identified increasing chaos is a result of the increased sympathetic activity in the patient, the combining resulting in a more accurate determination that the identified increasing chaos is a result of the increased sympathetic activity, more accurate than either the identified increasing chaos or the identified non-increasing parasympathetic activity alone;
detecting the physiological abnormality wherein the detected physiological abnormality is of a type detectable by the increased sympathetic activity in the patient; and
generating a signal indicative of the detected physiological abnormality.

41. The computer readable storage medium of claim 40, wherein the instructions for measuring comprise instructions for:
measuring a quantifiable characteristic of a heart of a patient with a heart sensor, wherein the instructions for quantifying the chaos comprise instructions for:
generating a sequence of values representative of the characteristic of the heart; and
selecting a first measurement time window corresponding to a first selected set of values within the sequence of values, wherein the instructions for identifying the increased chaos comprise instructions for:
analyzing the first selected set of values to identify the increasing chaos, wherein the instructions for identifying the non-increasing parasympathetic activity comprise instructions for:
selecting a second measurement time window corresponding to a second selected set of values within the sequence of values;
analyzing the second selected set of values to generate a power spectrum;
selecting a portion of the power spectrum; and
analyzing the selected portion of the power spectrum to identify the non-increasing parasympathetic activity.

* * * * *

UNITED STATES PATENT AND TRADEMARK OFFICE
CERTIFICATE OF CORRECTION

| | |
|---|---|
| PATENT NO. | : 9,737,258 B2 |
| APPLICATION NO. | : 13/755345 |
| DATED | : August 22, 2017 |
| INVENTOR(S) | : Chi-Sang Poon et al. |

It is certified that error appears in the above-identified patent and that said Letters Patent is hereby corrected as shown below:

Column 3, Line 5, delete "noise" and replace with --noise.--.

Column 3, Line 51, delete "heart beats" and replace with --heartbeats--.

Column 6, Line 66, delete "heart beats" and replace with --heartbeats--.

Column 7, Line 3, delete "heart beats" and replace with --heartbeats--.

Column 7, Line 6, delete "heart" and replace with --heart- --.

Column 9, Line 2, delete "characteristic" and replace with --characteristics--.

Column 9, Line 15, delete "HZ" and replace with --Hz--.

Column 11, Line 11, delete "long term" and replace with --long-term--.

Column 15, Line 31, delete "failure)." and replace with --failure.--.

Column 16, Line 25, delete "Natick, Mass." and replace with --Natick, MA--.

Column 16, Line 51, delete "events per hour," and replace with --events per hour;--.

Column 17, Line 47, delete "vertical axes" and replace with --vertical axis--.

Column 17, Line 55, delete "vertical axes" and replace with --vertical axis--.

Column 18, Line 24, delete "negative predictivity)" and replace with --negative predictivity.--.

Signed and Sealed this
Eighth Day of January, 2019

Andrei Iancu
*Director of the United States Patent and Trademark Office*

Column 20, Line 55, delete "log $e$" and replace with --log $\epsilon$--.

Column 24, Line 40, delete "(a)" and replace with --($\sigma$)--.